US007494980B2

(12) United States Patent
Leung et al.

(10) Patent No.: US 7,494,980 B2
(45) Date of Patent: Feb. 24, 2009

(54) ANTIMICROBIAL PEPTIDE AND METHODS OF USE THEREOF

(75) Inventors: Kai P Leung, Libertyville, IL (US); Sean P Concannon, St. Louis, MO (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 381 days.

(21) Appl. No.: 10/795,514

(22) Filed: Mar. 9, 2004

(65) Prior Publication Data

US 2004/0224897 A1 Nov. 11, 2004

Related U.S. Application Data

(60) Provisional application No. 60/455,206, filed on Mar. 10, 2003.

(51) Int. Cl.
*A61K 38/08* (2006.01)
*A61K 9/68* (2006.01)
*A61K 9/20* (2006.01)
*C07K 7/04* (2006.01)

(52) U.S. Cl. .................. 514/15; 530/328; 424/440; 424/441; 424/464

(58) Field of Classification Search .................. None
See application file for complete search history.

(56) References Cited

U.S. PATENT DOCUMENTS

| 5,989,522 | A | 11/1999 | Friedman |
| 6,365,130 | B1 | 4/2002 | Barry et al. |
| 6,365,635 | B1 | 4/2002 | Nomura et al. |
| 6,414,035 | B1 | 7/2002 | Vargas Munita et al. |
| 6,464,962 | B2 | 10/2002 | Heckendorn et al. |
| 6,503,539 | B2 | 1/2003 | Gestrelius et al. |

OTHER PUBLICATIONS

B.F. Gooch, et al. Am. J. Prev. Med. (2002) 23(18), pp. 55-80.*
NIH RFA DE-98-006: "Targeted Research on Oral Microbial Biofilms" Mar. 6, 1998.*
S.P. Concannon, et al. J. Med. Microbiol. (2003) 52, pp. 1083-1093.*
Bateman, Andrew et al., "The Isolation and Identification of Multiple Forms of the Neutrophil Granule Peptides from human Leukemic Cells", J Biol Chem, Apr. 25, vol. 266, 1991, pp. 7524-7530.
Blondelle, Sylvie E. et al., "Novel Antimicrobial Compounds Identified Using Synthetic Combinatorial Library Technology", Trends in Biotechnology, 1996, vol. 14, pp. 60-65.
Blondelle, Sylvie E. et al., "Identification of Antimicrobial Peptides by Using Combinatorial Libraries Made Up of Unnatural Amino Acids", Antimicrobial Agents and Chemotherapy, Oct. 1994, vol. 38, No. 10, pp. 2280-2286.
Blondelle, Sylvie E. et al., "Synthetic Combinatorial Libraries: Novel Discovery Strategy for Identification of Antimicrobial Agents", Antimicrobial Agents and Chemotherapy, May 1996, vol. 40, No. 5, pp. 1067-1071.
Blondelle, Sylvie E. et al., "Rapid Identification of Compounds with enhanced Antimicrobial Activity by Using Conformationally Defined Combinatorial Libraries", Biochem. J, 1996, vol. 313, pp. 141-147.
Boggiano, César, "Successful Identification of Novel Agents to Control Infectious Diseases from Screening Mixture-Based Peptide Combinatiorial Libraries in Complex Cell-Based Bioassays".
Boman, Hans G., "Antibacterial Peptides: Key Componets Needed in Immunity", Cell, Apr. 19, 1991, vol. 65, pp. 205-207.
Boman, Hans G., "Gene-Encoded Peptide Antibiotics and the Concept of Innate Immunity; An Update Review", Scand. J. Innunol., 1998, vol. 48, pp. 15-25.
Bowden, G. H. W., "Which Bacteria are Cariogenic in Humans?", Risk markers for Oral Diseases, vol. 1, Dental Caries, 1991, Cambridge University Press, Cabridge, UK, pp. 266-286.
Chen, Jie et al., "Development of Protegrins for the Treatment and Prevention of Oral Mucositis: Structure-Activity Relationships of Synthetic Protegrin Analogues", Biopolymers (Peptide Science), 2000, vol. 55, pp. 88-98.
Concannon, Sean P. et al., "Susceptibility of Oral Bacteria to an Antimicrobial Decapeptide", Journal of Medical Microbiology, 2003, vol. 52, pp. 1083-1093.
Davies, Julian, "Inactivation of Antibiotics and the Dissemination of Resistance Genes", Science, Apr. 15, 1994, vol. 264, pp. 375-381.
Decker, Thomas et al., "A Quick and Simple Method for the Quantitation of Lactate Dehydorgenase Release in Measurements of Cellular Cytotoxicity and Tumor Necrosis Factor (TNF) Activity". Journal of Immunological Method, 1988, vol. 15, pp. 61-69.
Donlan, Rodney M. et al, "Biofilms: Survival Mechanisms of Clinically Relevant Microorganims", Clinical Mirobiology Reviews, Apr. 2002, vol. 15, No. 2, pp. 167-193.
Dyson H. Jane et al., "Defining Solution Conformations of Small Linear Peptides", Annu. Rev. Biophys. Biophys. Chem., 1991, vol. 20, pp. 519-538.
Elsbach, Peter, "What is the Real Role of Antimicrobial Polypeptides that can Mediate Several Other Inflammatory Responses?", The Journal of Clinical Investigation, Jun. 2003, vol. 111, No. 11, pp. 1643-1645.
Friedrich, Carol et al., "Salt-Resistant Alpha-Helical Cationic Antimicrobial Peptides", Antimicrobial Agents and Chemotherapy, Jul. 1999, vol. 43, No. 7, pp. 1542-1548.
Fuchs, Peter C. et al., "In Vitro Antimicrobial Activity of MSI-78, a Magainin Analog", Antimicrobial Agents and Chemotherapy, May 1998, vol. 42, No. 5, pp. 1213-1216.

(Continued)

*Primary Examiner*—Andrew D Kosar
(74) *Attorney, Agent, or Firm*—Elizabeth Arwine

(57) ABSTRACT

A method of preventing biofilm formation in an environment including the steps of administering to the environment an effective amount of a peptide having the amino acid sequence $NH_2$-lys-lys-val-val-phe-lys-val-lys-phe-lys-$CONH_2$ [SEQ ID NO: 1] The method is useful in preventing the formation of biofilms in various environments including a home, workplace, laboratory, industrial environment, aquatic environment, animal body or human body. A method of inhibiting the growth of oral microorganisms including the steps of administering to an oral environment an effective amount of a peptide having the amino acid sequence $NH_2$-lys-val-val-phe-lys-val-lys-phe-lys-$CONH_2$ [SEQ ID NO: 1].

16 Claims, 13 Drawing Sheets
(6 of 13 Drawing Sheet(s) Filed in Color)

OTHER PUBLICATIONS

Gibbons, R. J., "Role of Adhesion in Microbial Colonization of Host Tissues: A Contribution of Oral Microbiology", J. Dent Res, 1996, vol. 3, pp. 866-870.

Guthmiller, Janet J. et al., "Susceptibilities of Oral Bacteria and Yeast to Mannalian Cathelicidins", Antimicrobial Agents and Chemotherapy, Nov. 2001, vol. 45, No. 11, pp. 3216-3219.

Hancock, Robert E. W., "Antibacterial Peptides and the Outer Membranes of Gram-Negative Bacilli", J. Med. Microbiol (Editorial), 1997, vol. 46, pp. 1-3.

Hancock, Robert E. W., "Peptide Antibiotics", The Lancet, Feb. 8, 1997, vol. 349, pp. 418-422.

Hancock, Robert E. W. et al., "Cationic Peptides: A New Source of Antibiotics", TIBTECH, Feb. 1998, vol. 16, pp. 82-88.

Hancock, Robert E. W. et al., "Peptides Antibiotics", Antimicrobial Agents and Chemotherapy, Jun. 1990, vol. 43, No. 6, pp. 1317-1323.

Hancock, Robert E. W. et al., "Role of Membranes in the Activities of Antimicrobial Cationic Peptides", FEMS Microbiology Letters 206, 2002, pp. 143-149.

Hancock, Robert E. W. et al., "Cationic Bactericidal Peptides", Advances in Microbial Physiology, 1995, vol. 37, pp. 135-175.

Helmerhorst, Eva J. et al., "Synthetic Histatin Analogues with Broad-Spectrum Antimicrobial Activity", Biochem. J., 1997, vol. 325, pp. 39-45.

Helmerhorst, Eva J. et al., "The Effects of Histatin-Derived Basic Antimicrobial Peptides on Oral Biofilms", J. Dent Res, Jun. 1999, vol. 78, No. 6, pp. 1245-1250.

Henderson et al., "Bacteria-Cytokine Interactions in Health and Disease", Portland Press, pp. 351-354.

Hong, Sung Y. et al., Identification and Characterization of Novel Antimicrobial Decapeptides Generated by Combinatiorial Chemotherapy, Oct. 1998, vol. 42, No. 10, pp. 2534-2541.

Kaiser, E. et al., "Color Test for Detection of Free Terminal Amino Groups in the Solid-Phase Synthesis of Peptides", Short Communications, Oct. 1969, pp. 595-599.

Kilian, Mogens et al., "Taxonomic Study of Viridans Streptococci: Description of Stretococcus gordonii sp. Nov. and Emended Descriptions of Streptococcus sanguis (White and Niven 1946), Streptococcus oralis (Bridge and Sneath 1982), and Streptococcus mitis (Andrewes and Hordes 1906)", International Journal of Systematic Bacterilogy, Oct. 1989, vol. 39, No. 4, pp. 471-484.

Koczulla, Andreas R. et al., "Antimicrobial Peptides—Current Status and Therapeutic Potential", Drugs, 2003, Vo. 63, No. 4, pp. 389-406.

Koczulla, Rembert et al., "An Angiogenic Role for the Human Peptide Antibiotic LL-37/hCAP-18", The Journal of Clinical Investigation, Jun. 2003, vol. 111, No. 11, pp. 1665-1672.

Kolenbrander, Paul E., "Adhere Today, Here Tomorrow; Oral Bacterial Adherence", Journal of Bacteriology, Jun. 1993, vol. 175, No. 11. pp. 3247-3252.

Kolenbrander, Paul E., "Coaggregation: Specific Adherence Among Human Oral Plaque Bacteria", The FAEB Journal, Mar. 1993, vol. 7, pp. 406-413.

Lee, In Hee et al., "Effects of pH and Salinity on the Antimicrobial Properties of Clavanins", Infection and Immunity, Jul. 1997, vol. 65, No. 7, pp. 2898-2903.

Lisle, John T. et al., "Fluorescent Probes Applied to Physiological Charcterization of Bacterial Biolfilms", Methods in Enzymology, 1999, vol. 310, pp. 166-178.

Loesche, W. J. et al., "Bacteriology of Human Experimental Gingivitis: Effects of Plaque and Gingivitis Score", Infection and Immunity, Sep. 1978, vol. 21, pp. 830-839.

Mackay, Bruce J., et al., "Growth-Inhibitory and Bactericidal Effects of Human Parotid Salivary Histidine-Rich Polypeptides on Streptococcus mutans", Infection and Immunity, Jun. 1984, vol. 44, No. 3, pp. 695-701.

Marsh, P. D. et al., "Dental Plaque as Biofilm", Journal of Industrial Microbiology, 1995, vol. 15, 169-175.

Mickels, Nancy et al., "Clinical and Microbial Evaluation of a Histatin-containg Mouthrinse in Humans with Experimental Gingivitis", Journal of Clinical Periodontology, May 2001, vol. 28, No. 5, pp. 404-410.

Miyasaki, Kenneth T. et al., "Killing of Oral, Gram-Negative, Facultative Bacteria By the Rabbit Defensin, NP-1", Oral Microbiol Innunol, 1990, vol. 5, pp. 315-319.

Miyasaki, Kenneth T. et al., "Sensitivity of Periodontal Pathogens to the Bactericidal Activity of Synthetic Protegrins, Antibiotic Peptides Derived from Porcine Leukocytes", J. Dent Res, Aug. 1997, vol. 76, No. 8, pp. 1453-1459.

Miyasaki, Kenneth T. et al., "Killing of Fusobacterium Nucleatum, Porphyromonas Gingivalis and Prevotella Intermedia by Protegrins", Journal of Periodontal Research, 1998, vol. 33, pp. 91-97.

Mosca, Deborah A. et al., "IB-367, A Protegin Peptide with In Vitro and In Vivo Activities Against the Microflora Associated with Oral Mucositis", Antimicrobial Agents and Chemotherapy, Jul. 2000, vol. 44, No. 7, pp. 1803-1808.

Mosmann, Tim, "Rapid Colorimetric Assay for Cellular Growth and Survival: Application to Proliferation and Cytotoxicity Assays", Journal of Immunological Methods, 1983, vol. 65, pp. 55-63.

Murakami, M. et al., "Cathelicidin Antimicrobial Peptides are Expressed in Salivary Glands and Saliva", J Dent Res, 2002 vol. 81, No. 12, pp. 845-850.

Nizet, Victor et al., "Innate Antimicrobial Peptide Protests the Skin from Invasive Bacterial Infection", Naure, Nov. 22, 2001, vol. 414, pp. 454-457.

Oh, J. E. et al., "Structure-Activity Relationship Study: Short Antimicrobial Peptides", The Journal of Peptide Reseach, January 199, vol. 53, No. 1, pp. 41-46.

Pardi, A. et al., "Calibration of the Angular Dependence of the Amide Proton-$C^°$ Proton Coupling Constants, $^3J_{HN\alpha}$, in a Globular Protein—Use of $^3J_{HN\alpha}$ for Identification of Helical Secondary Structure", J. Mol, Biol. Jan. 1984, vol. 180, pp. 741-751.

Raj, Periathamby A. et al., "Salivary Histatin 5: Dependence of Sequence, Chain Length, and Helical Conformation for Candidacidal Activity", The Journal of Biological Chemistry, Mar. 5, 1990, vol. 265, No. 7, pp. 3898-3905.

Raj, Periathamby A. et al., "Delineation of an Active Fragment and Poly(L-proline) II Conformation for Candidacidal Activity of Bactenecin 5", Biochemistry, 1996, vol. 35, pp. 4314-4325.

Raj, Periathamby A. et al., "Structure of Human Salivary Histatin 5 in Aqueous and Nonaqueous Solutions", Biopolymers, 1998, vol. 45, pp. 51-67.

Raj, Periathamby A. et al., "Synthesis, Microbicidal Activity, and Solution Structure of the Dodecapeptide from Bovine Neutrophils", Biopolymers, 2000, vol. 53, pp. 281-292.

Raj, Periathamby A. et al., "Large-scale Synthsis and Functional Elements for the Antimicrobial Activity of Defensins", Biochem. J., 2000, vol. 347, pp. 633-641.

Rothstein, David M. et al., "Anticandida Activity Is Retained in P-113, a 12-Amino-Acid Fragment of Histatin 5", Antimicrobial Agents and Chemotherapy, May 2001, vol. 45, No. 5, pp. 1367-1375.

Schutze, G. E. et al., "Resistant Pneumococcus: A Worldwide Problem", Infection, 1994, vol. 22, No. 4, pp. 233-237.

Slots, J. et al., "The Occurrence of Actinobacillus Actinomycetemcomitans, Bacteroides Gingivalis and Bacteroides Intermedius in Destructive Periodondal Disease in Adults", Journal of Clinical Periodontology, 1986, vol. 13, pp. 570-577.

Socransky, S. S. et al., "Microbial Complexes in Subgingival Plaque", Journal of Clinical Periodontology, 1998, vol. 25, pp. 134-144.

Sumney, David L. et al., "Charatcterization of Bacteria Isolated from Human Root Surface Carious Lesions", J Dent Res, Mar.-Apr. 1974, vol. 53, No. 2, pp. 343-351.

Tamamura, Hirokazu et al., "Synthesis of Protegrin-Related Peptides and Their Antibacterial and Anti-human Immunodeficiency Virus Activity", Chem. Pharm. Bull. 1995, Vo. 43, No. 5, pp. 853-858.

Tanaka, D. et al., "Sensitivity of Actinobacillus Actinomycetemcomitans and Capnocytophaga spp. To the Bactericidal Action of LL-37: a Cathelicidin Found In Human Leukocytes and Epithelium", Oral Microbiol Immunol, 2000, vol. 15, pp. 226-231.

Van Houte, J., "Role of Micro-Organisms in Caries Etiology", J Dent Res, Mar. 1994, vol. 73, No. 3, pp. 672-681.

Wade, D. et al., "Antibacterial Peptides Designed as Analogs or Hydbrids of Cecropins and Melittin", Int. J. Peptide Protein Res., 1992, vol. 40, pp. 429-436.

Wüthrich, Kurt, "NMR of Proteins and Nucleic Acids", 1986, John Wiley & Sons, Inc., New York, pp. 44-92 and 117-199.

Yeaman, Michael R. et al., "Mechanisms of Antimicrobial Peptide Action and Resistance", The Pharmacological Reviews, 2003, vol. 55, No. 1, pp. 27-55.

Zasloff, Michael, "Antibiotic Peptides as Mediators of Innate Immunity", Current Opinion in Immunology, 1992, vol. 4, pp. 3-7.

Zasloff, Micahel, "Antimicrobial Peptides of Multicellular Organisms", Nature, Jan. 2002, vol. 415, pp. 389-395.

Zhao, Chengquan et al., "Identification of a New Member of the Protegrin Family by cDNA Cloning", FEBS Letters, 1994, vol. 346, pp. 285-288.

Lee,Sung-Woo, "Effect of Chlorhexidine on Causative Micoorganisms of Infective Endocarditis in Oral Cavity", The Korean Academy of Oral Medicine, printed from www.kaom.org/iour/1996-1/io96-1-1.htm, 1996, vol. 21, No. 1, pp. 1-2.

Modesto, A. et al., "Fluoride Release; Composites; Glass Ionomers; Acidulated Phosphate Fluoride Gel", Journal of Dentistry for Children, Sep.-Oct. 2000, vol. 67, abstract from ASDC Journal abstracts.

Oh, J. E. et al., "Design, Synthesis and Characterization of Antimicrobial Pseudopeptides Corresponding to Membrane-active Peptide", Journal of Peptide Research, 1999, vol. 54, pp. 129-136.

Tsitsika, Artemis et al., "Single-Oral-Dose Azithromycin Prophylaxis against Experimental Streptococcal or Staphylococcal Aortic Valve Endocarditis", Antimicrobial Agents and Chemotherapy, Jun. 2000, vol. 44, No. 6, pp. 1754-1756.

* cited by examiner

|  | 1 | 2 | 3 | 4 | 5 | 6 | 7 | 8 | 9 | 10 |
|---|---|---|---|---|---|---|---|---|---|---|
| KSL | K | K | V | V | F | K | V | K | F | K |
| $J_{NH-C^{\alpha}H}$ |  | 6.8 | 7.5 | 8.1 | 7.4 | 7.5 | 7.3 | 7.5 | 6.8 | 7.6 |
| $d\delta/dT$ (p.p.m. $K^{-1} \times 10^{-3}$) |  | 5.2 | 5.0 | 4.7 | 4.2 | 4.4 | 4.6 | 4.5 | 4.8 | 4.3 |
| NH |  |  |  |  | • |  | • |  | • |  |
| $\alpha N\ (i, i+1)$ | —————————————————————— |
| $\alpha N\ (i, i)$ | ——————————————  ———— |
| $\beta N\ (i, i)$ | ——————————————————— |
| $\alpha\beta\ (i, i)$ | ——————————————  ———— |

FIGURE 2a

|  | 1 | 2 | 3 | 4 | 5 | 6 | 7 | 8 | 9 | 10 |
|---|---|---|---|---|---|---|---|---|---|---|
| KSL | K | K | V | V | F | K | V | K | F | K |
| $J_{NH-C^{\alpha}H}$ |  | 7.5 | 6.8 | 6.9 | 5.8 | 5.4 | 5.8 | 5.9 | 5.7 | 5.2 |
| $d\delta/dT$ (p.p.m. $K^{-1} \times 10^{-3}$) |  | 5.2 | 5.0 | 4.7 | 2.9 | 2.4 | 2.6 | 2.5 | 2.2 | 2.3 |
| NH |  |  |  |  | • | • | • | • | • | • |
| $\alpha N\ (i, i+3)$ | ———————————————————— |
| $NN\ (i, i+1)$ | ——————————————————— |
| $\alpha\beta\ (i, i+3)$ | (stepped series of lines) |

FIGURE 2b

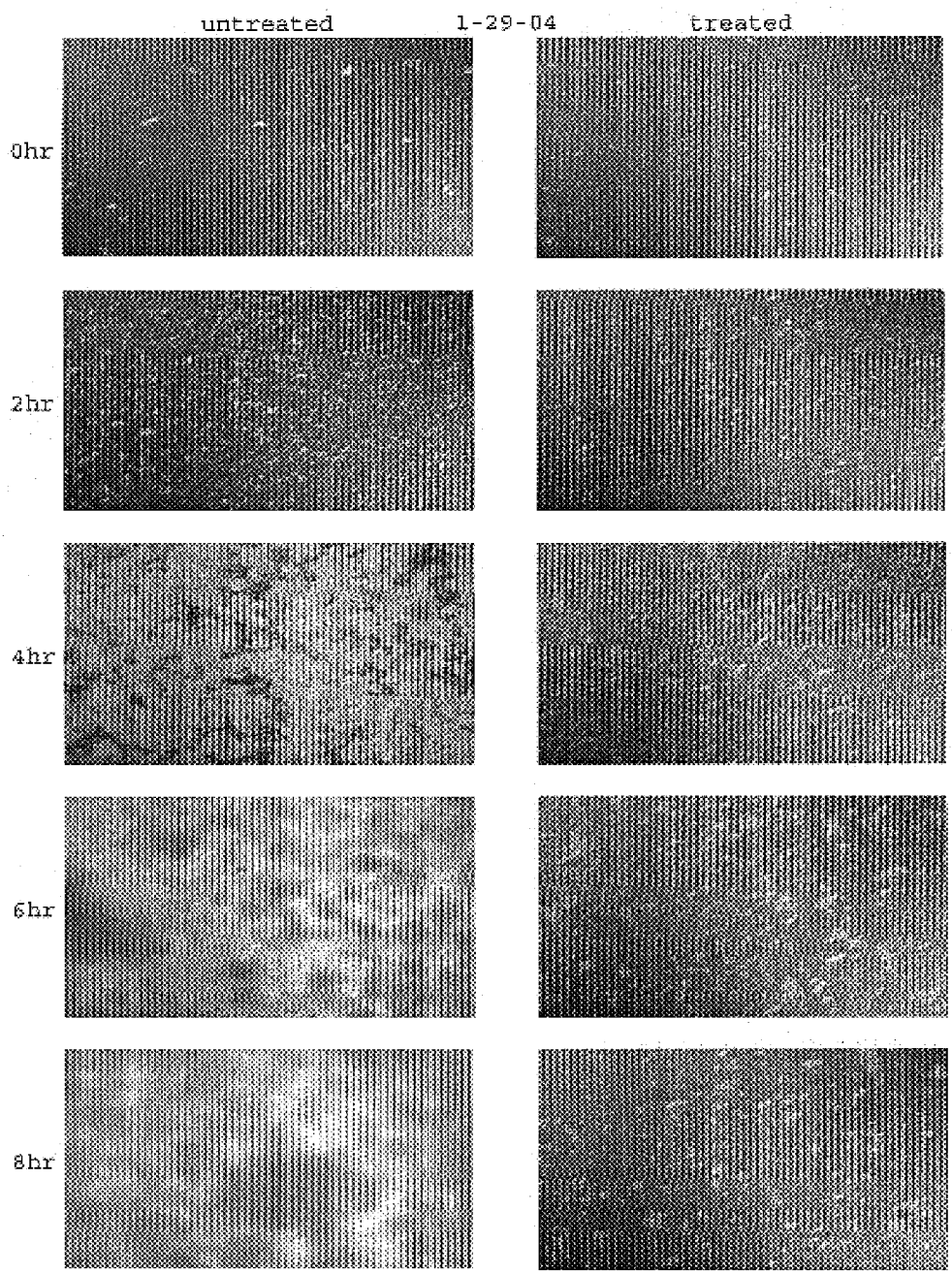
FIGURE 13a                    FIGURE 13b

ANTIMICROBIAL PEPTIDE AND METHODS OF USE THEREOF

This application claims priority pursuant to 35 U.S.C. 119 (e) to U.S. Provisional Application No. 60/455,206, filed Mar. 10, 2003.

I. FIELD OF THE INVENTION

This invention relates generally to the field of antimicrobial peptides. More particularly, the present invention relates to the use of an antimicrobial peptide in the prevention of biofilm formation and for inhibiting the growth of oral microorganisms.

II. BACKGROUND OF THE INVENTION

The efficacy of conventional antibiotics has declined in recent years due to the progressive increase and proliferation of antibiotic-resistant organisms (Davies, 1994; Schutze et al., 1994). The discovery of a large number of naturally occurring invertebrate and vertebrate antimicrobial peptides has resulted in the emergence of novel classes of peptide antibiotics that exhibit remarkable selectivity for prokaryotes and minimize problems of introducing microbial resistance (Boman, 1998; Hancock & Lehrer, 1998; Hancock & Chapple, 1999; Nizet et al., 2001; Zasloff, 2002). These peptide antibiotics interact directly with microbial surfaces, often leading to the formation of pores or in some way compromising membrane permeability (Zasloff, 1992; Hancock, 1997a; Hancock & Rozek, 2002; Koczulla & Bals, 2003; Yeaman & Yount, 2003). Such molecules exhibit diverse structures; however, most are cationic amphiphilic molecules because of the presence of arginine and lysine residues and can be classified into four or five different structural groupings. These include: (a) cysteine-rich, amphiphilic β-sheet peptides (α- and β-defensins, protegrins, and tachyplesins); (b) cysteine-disulfide ring peptides with or without amphiphilic tails (bactenecin, ranalexin, and brevinins); (c) amphiphilic α-helical peptides without cysteine (magainins and cecropins); and (d) linear peptides with one or two predominant amino acids (proline or tryptophan) (Hancock et al., 1995; Hancock, 1997b; Hancock & Lehrer, 1998; Henderson et al., 1998).

Many synthetic analogs to these peptides have been created in attempts to improve the antimicrobial activity of some of these naturally occurring antibacterial peptides (Wade et al., 1992, Tamamura et al., 1995; Helmerhorst et al., 1997; Fuchs et al., 1998; Chen et al., 2000; Mosca et al., 2000; Rothstein et al., 2001). For example, Dhvar 5, an analog of histatin 5, one of the antimicrobial histatin peptides that are derived from saliva (Helmerhorst et al., 1999; Mickels et al., 2001), and IB-367, an analog of protegrins, the antimicrobial peptides that were isolated form porcine leukocytes (Zhao et al., 1994; Chen et al., 2000; Mosca et al., 2000), are more effective in inhibiting bacterial growth and are easily synthesized as compared to their native counterparts. Although, new antimicriobial peptides have been developed, many of these peptides are large, complex, and are difficult and expensive to synthesize. Accordingly, a need exists for more effective and broad-spectrum antimicrobial peptides that are more easily synthesized. In particular, a need exists for an antimicrobial peptide that is effective in inhibiting the growth of various microorganisms that exist in the human mouth. In addition, a need exists for a peptide that is effective in preventing the formation of biofilms, which have been implicated in the development of infections and diseases such as gingivitis and various forms of periodontal diseases. In general, biofilms may include microorganisms such as bacteria, fungi, yeast, viruses and protozoa.

Typically, biofilms are not structurally homogeneous monolayers of microbial cells on a surface. Rather, they can be described as heterogeneous. Living, fully hydrated biofilms are composed of cells and matrix material, wherein the cells are located in matrix-enclosed "towers" and "mushrooms". Once a biofilm has formed and the matrix has been secreted by the sessile cells, the resultant structure is highly viscoelastic and behaves in a rubbery manner. (Donlan et al., 2002).

Biofilms form preferentially at high-shear locations in natural and industrial systems. Smooth surfaces are colonized just as easily as rough surfaces and the physical characteristics of a surface influence bacterial adhesion to only aminor extent. When biofilms are formed in low-shear environments, they have a low tensile strength and break easily, but biofilms formed at high shear locations are remarkably strong and resistant to mechanical breakage. (Donlan et al., 2002).

The nature of biofilm structures and the physiological attributes of biofilm organisms confer an inherent resistance to antimicrobial agents, whether these antimicrobial agents are antibiotics, disinfectants, or germicides. Mechanisms responsible for resistance may be one or more of the following: i) delayed penetration of the antimicrobial agent through the biofilm matrix, ii) altered growth rate of biofilm organisms, and iii) other physiological changes due to the biofilm mode of growth. For example, antimicrobial molecules must diffuse through the biofilm matrix in order to inactivate the encased cells. The extracellular polymeric substances constituting this matrix present a diffusional barrier for these molecules by influencing either the rate of transport of the molecule to the biofilm interior or the reaction of the antimicrobial material with the matrix material. Due to the strong resistance to antimicrobial agents that biofilms possess, it is essential to prevent the formation of biofilms before they can cause harm in an environment. (Donlan et al., 2002).

As described above, a biofilm is a complex, highly differentiated, multicultural community that has been shown to cause a variety of infections. The organisms responsible, the extracellular components of the biofilm, the nature of the required conditioning film, and the mode of pathogenicity vary from one disease condition to the next. In most cases, however, there are certain underlying processes that are unchanging: production of an extracellular matrix polymer, resistance to antimicrobial agents that increases with biofilm age, and resistance to immune system clearance. Examples of infections that biofilms have been associated with include, but are not limited to periodontitis, native valve endocarditis, otitis media, chronic bacterial prostatitis, and cystic fibrosis. (Donlan et al., 2002).

Periodontitis is one of the most prevalent infectious diseases in the world, affecting approximately forty-nine million people in the United States alone and 10-12% of the population in the industrialized countries. The following organisms have been isolated from patients with moderate periodontal disease and positively correlated with gingivitis: *Porphyromonas gingivalis; Tanarella forsythensis; Treponema denticola; Actinobacillus actinomycetemcomitans; Fusobacterium nucleatum, Peptostreptococcus micros, Eubacterium timidum, Eubacterium brachy, Lactobacillus* spp., *Actinomyces naeslundii, Pseudomonas anaerobius, Eubacterium* sp. strain D8, *Prevotella intermedia, Fusobacterium* sp., *Selenomonas sputigena, Eubacterium* sp. strain D6, *Bacteroides pneumosintes*, and *Haemophilus aphrophilus*. (Donlan et al., 2002; Socransky et al., 1998).

Proteinaceous conditioning films, called acquired pellicle, develop on exposed surfaces of tooth enamel almost immediately after cleaning of the tooth surface within the oral cavity. The pellicle comprises albumin, lysozyme, glycoproteins, phospoproteins, lipids, and gingival crevice fluid. Within hours of pellicle formation, single cells of primarily gram-positive cocci and rod-shaped bacteria from the normal oral flora colonize these surfaces. The pioneer species are predominantly streptococci, actinomycetes, and smaller numbers of *Haemophilus*. These organisms have the ability to bind directly to the pellicle through surface proteinaceous appendages and the production of extracellular glucans. After several days, actinomycetes predominate, and the characteristic polysaccharide matrix of a biofilm begins to develop. (Donlan et al., 2002; Marsh et al., 1995).

Organisms associating with and attaching to cells in this early biofilm do so by a process called coaggregation. Coaggregation is cell-to-cell recognition whereby organisms in the biofilm can recognize and adhere to genetically distinct bacteria by means of adhesions. These adhesions recognize protein, glycoprotein, or polysaccharide receptors on oral surfaces, including other cell types. A climax biofilm community, termed plaque, will devlop within 2 to 3 weeks if the plaque is left undisturbed, with 50 to 100 µm thick bioflims developing. However, it is possible for plaque to form within 24 hours. In addition to matrix polysaccharides, there will be polymers of salivary origin. (Donlan et al., 2002; Kolenbrander et al., 1999).

Plaque that becomes mineralized with calcium and phosphate ions is termed calculus or tartar. In addition to development on the tooth surfaces (within fissures), plaque can develop more extensively in protected areas, including approximal areas (between the teeth) and the gingival crevice (between the tooth and gum). As the plaque mass increases in these protected areas, the beneficial buffering and antimicrobial properties of the saliva are less able to penetrate and protect the tooth enamel, leading to dental caries or periodontal disease. (Donlan et al., 2002).

As the organisms develop biofilms in the subgingival crevice, they produce proteolytic enzymes that damage tissue directly or interfere with host defenses. Collangenase and hyaluronidase are also present and capable of degrading collagen. Breakdown of the fiber barrier system may occur, and the lesion may then progress to one that may attack the supporting structures of the tooth. Gram-negative organisms also produce endotoxins that may result in inflammation. It has been demonstrated that the periodontal pathogens *Porphyromonas gingivalis* and *Prevotella intermedia* are capable of invading epithelium cells in a laboratory assay, eliciting invasion mechanisms similar to those of other pathogens. (Donlan et al., 2002).

III. SUMMARY OF THE INVENTION

Accordingly, it is an object of the present invention to minimize or overcome the problems described above.

It is another object of this invention to provide novel and effective methods of using a peptide having broad-spectrum antimicrobial properties.

Another object of this invention is to provide novel and effective methods for the prevention and treatment of infections and/or diseases.

A further object of this invention is to provide methods of using a novel peptide in the prevention of biofilm formation.

Still another object of this invention is to provide methods of using a novel peptide to inhibit the growth of oral microorganisms.

Many of these objects are met by a method for preventing biofilm formation in an environment. The present invention contemplates the steps of administering to the environment an effective amount of a peptide having the amino acid sequence lys-lys-val-val-phe-lys-val-lys-phe-lys (SEQ ID NO: 1), wherein the formation of a biofilm in the environment is effectively prevented.

The method of the present invention may be used to minimize and, preferably, prevent the formation of biofilms in a variety of environments including, but not limited to household, workplace, laboratory, industrial, and aquatic environments. For example, bacterial biofilms are known to cause serious problems in industrial water systems, such as pipeline systems. In addition, the method of the present invention may be used to prevent the formation of a biofilm in a human body or animal body, especially in the treatment of infections. For example, the present invention is effective in the prevention of biofilms in oral environments such as a human or animal mouth. The method of the present invention may be used to prevent the formation of plaque or caries on a human tooth. New methods for the direct examination of biofilms have shown that the organisms that cause many medical and dental device-related infections actually grown in biofilms in or on these devices.

A biofilm deterring peptide may be administered to the target environment via topical application including transdermal application, spray, aerosol, injection, ingestion or inhalation. In addition, when administered to humans or animals, the peptide can be administered by any known method, including but not limited to topical application such as transdermal application, orally, nasally, intraveneously, and intraperitoneally, etc. Furthermore, various carriers may be used to administer the antimicrobial peptide to the environment. These carriers include, but are not limited to films or tapes, gels, microspheres such as hydrogel microspheres, lozenges, chewing gum, and dentifrices.

The present invention is also related to a method of inhibiting the growth of oral microorganisms in an oral environment including the steps of administering to the environment an effective amount of a peptide having the amino acid sequence lys-lys-val-val-phe-lys-val-lys-phe-lys (SEQ ID NO: 1). The antimicrobial peptide may be administered to the oral environment by any known method, including but not limited to topical application, spray, aerosol, injection, ingestion or inhalation.

The oral environment may be a human or animal mouth. The method of the present invention is effective in treating or preventing various oral infections, including, but not limited to gingivitis, various forms of periodontitis, and mucositis. For example, the method of the present invention is effective in preventing the development of plaque or caries on teeth.

The antimicrobial peptide, lys-lys-val-val-phe-lys-val-lys-phe-lys (SEQ ID NO: 1) (hereafter, as applicable, referred to as "KSL"), used in the methods of the present invention has been shown to possess a broad range of antimicrobial activity. Specifically, the peptide is effective in inhibiting the growth of methicillin-resistant *Staphylococcus aureus* (MRSA), *Pseudomonas aeruginosa* and a number of enterics. In addition, the peptide used in the methods of the present invention has been shown to irreversibly inhibit the growth of *Candida albicans* suggesting that this agent also possesses antifungal activity. (Hong et al., 1998)

Furthermore, it has been demonstrated that KSL: i) is effective in inhibiting the growth of a broad range of laboratory strains of oral bacteria; (ii) at higher concentrations, is capable of reducing viable counts of members of resident saliva bacteria collected from healthy human subjects; and iii)

did not show any cytotoxic effects against human gingival fibroblasts (HGF) (Concannon et al, 2003). The peptide has been shown to inhibit the growth of oral bacteria/pathogens that are involved in the development of caries. For example, growth of *Actinomyces naeslundii*, a putative pathogen that is involved in the development of gingivitis (Loesche & Syed, 1978) and root-surface caries (Summey & Jordan, 1974) and is an early colonizer for plaque formation (Kolenbrander et al., 1993; Gibbons, 1996) was inhibited by KSL at a fairly low concentration, i.e. 3.13 μg ml$^{-1}$. Similarly, growth of *S. mutans* ATCC (American Type Culture Collection) 25175$^T$ and *L. acidophilus*, cariogenic organisms (Bowden, 1991; van Houte, 1994), was inhibited by KSL at concentrations of <10 μg ml$^{-1}$. In addition, growth of members of the *S. oralis* group, including *S. sanguis, S. gordoni* and *S. mitis*, was inhibited by KSL, with Minimum Inhibitory Concentrations (MICs) that ranged from 25 to 50 μg ml$^{-1}$ (Concannon et al., 2003). Members of the *S. oralis* group, together with *Actinomyces naeslundii* as described above, are primary colonizers of the cleaned tooth and can undergo intra- and intergeneric co-aggregation with a range of partner organisms in vivo, which contributes to plaque accumulation. The observation that KSL at 50 μg ml$^{-1}$, or below was inhibitory in vitro to growth of members of the *S. oralis* group, *Actinomyces naeslundii* and the major cariogenic pathogens suggests that KSL would be effective in controlling the formation of plaque and dental caries in vivo. This is supported by the observation that KSL, at higher concentrations, caused significant reductions in viable counts of resident saliva bacteria. This is particularly relevant as saliva bacteria are released from biofilms formed on hard and soft tissues in the oral cavity (Helmerhorst et al., 1999). Furthermore, it has been shown that these saliva bacteria or bacteria collected from plaque are more resistant to antimicrobial peptides than pure cultures of oral bacteria (Helmerhorst et al., 1999). This may be one of the reasons why higher concentrations of antimicrobials are needed to inhibit the growth of resident saliva bacteria, as also shown in the present application.

DEFINITIONS AND ABBREVIATIONS

The term "antimicrobial" as used herein means the killing of microorganisms or the suppression of their multiplication and/or growth.

The term "biofilm" as used herein means a mixed population of microorganisms that grow on surfaces. The microorganisms may include, but are not limited to bacteria, fungi, protozoa, viruses and yeast.

As used herein, "Minimum Bactericidal Concentration" or "MBC" means the lowest concentration of antimicrobial agent to prevent visible growth of a tested microorganism as revealed by plating on the surface of nutrient agar or in nutrient broth.

As used herein, "Minimum Inhibitory Concentration" or "MIC" means the smallest amount of antimicrobial agent needed to inhibit the growth of a microorganism as reflected by the prevention of visible turbidity of the tested microorganism.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

"Oral microorganism" as used herein, means any living organism of microscopic size that exists in the mouth. The microorganisms may include bacteria, fungi, yeast, viruses or protozoa.

TECHNICAL REFERENCES

Bateman, A., Singh, A., Shustik, C., Mars, W. M. & Solomon, S. (1991) "The isolation and identification of multiple forms of the neutrophil granule peptides from human leukemic cells" *J Biol Chem* 266, 7524-7530.

Blondelle, S. E. & Houghten, R. A. (1996) "Novel antimicrobial compounds identified using synthetic combinatorial library technology" *Trends Biotechnol* 14, 60-65.

Blondelle, S. E., Takahashi, E., Weber, P. A. & Houghten, R. A. (1994) "Identification of antimicrobial peptides by using combinatorial libraries made up of unnatural amino acids" *Antimicrob Agents Chemother* 38, 2280-2286.

Blondelle, S. E., Perez-Paya, E. & Houghten, R. A. (1996a) "Synthetic combinatorial libraries: novel discovery strategy for identification of antimicrobial agents" *Antimicrob Agents Chemother* 40, 1067-1071.

Blondelle, S. E., Takahashi, E., Houghten, R. A. & Perez-Paya, E. (1996b) "Rapid identification of compounds with enhanced antimicrobial activity by using conformationally defined combinatorial libraries" *Biochem J* 313, 141-147.

Boggiano, C., Reixach, N., Pinilla, C. & Blondelle, S. E. (2003) "Successful identification of novel agents to control infectious diseases from screening mixture-based peptide combinatorial libraries in complex cell-based bioassays" *Biopolymers* 71, 103-116.

Boman, H. G. (1991) "Antibacterial peptides: key components needed in immunity" *Cell* 65, 205-207.

Boman, H. G. (1998) "Gene-encoded peptide antibiotics and the concept of innate immunity: an update review" *Scand J Immunol* 48, 15-25.

Bowden, G. H. W. (1991) "Which bacteria are cariogenic in humans? Risk Markers for Oral Diseases" vol. I, pp. 266-286. Edited by N. W. Johnson. Cambridge, UK: Cambridge University Press.

Chen, J., Falla, T. J., Liu, H. & 9 other authors (2000) "Development of protegrins for the treatment and prevention of oral mucositis: structure-activity relationships of synthetic protegrin analogues" *Biopolymers* 55, 88-98.

Concannon, S. P., Crowe, T. D., Abercrombie, J. J., Molina, C. M., Hou, P., Sukumaran, D. K., Raj, P. A., Leung, K. P. (2003) "Susceptibility of oral bacteria to an antimicrobial decapeptide" *J Med Microbiol* 52, 1083-1093.

Davies, J. (1994) "Inactivation of antibiotics and the dissemination of resistance genes" *Science* 264, 375-382.

Decker, T. & Lohmann-Mafthes, M. L. (1988) "A quick and simple method for the quantitation of lactate dehydrogenase release in measurements of cellular cytotoxicity and tumor necrosis factor (TNF) activity" *J Immunol Methods* 115, 61-69.

Donlan, R. M., Costerton, J. W. (2002) "Biofilms: Survival Mechanisms of Clinically Relevant Microorganisms" *Clin Microbiol Rev* 15 (2), 167-193.

Dyson, H. J. & Wright, P. E. (1991) "Defining solution conformations of small linear peptides" *Annu Rev Biophys Biophys Chem* 20, 519-538.

Elsbach, P. (2003) "What is the real role of antimicrobial polypeptides that can mediate several other inflammatory responses?" *J Clin Invest* 111, 1643-1645.

Friedrich, C., Scott, M. G., Karunaratne, N., Van, H. & Hancock, R. E. W. (1999) "Salt-resistant alpha-helical cationic antimicrobial peptides" *Antimicrob Agents Chemother* 43, 1542-1548.

Fuchs, P. C., Barry, A. L & Brown, S. D. (1998) "In vitro antimicrobial activity of MSI-78, a magainin analog" *Antimicrob Agents Chemother* 42, 1213-1216.

Gibbons, R. J. (1996) "Role of adhesion in microbial colonization of host tissues: a contribution of oral microbiology" *J Dent Res* 75, 866-870.

Guthmiller, J. M., Vargas, K. G., Srikantha, R., Schomberg, L. L., Weistroffer, P. L., McCray, P. B., Jr & Tack, B. F. (2001) "Susceptibilities of oral bacteria and yeast to mammalian cathelicidins" *Antimicrob Agents Chemother* 45, 3216-3219.

Hancock, R. E. W. (1997a) "Antibacterial peptides and the outer membranes of Gram-negative bacilli" *J Med Microbiol* 46, 1-3.

Hancock, R. E. W. (1997b) "Peptide antibiotics" *Lancet* 349, 418-422.

Hancock, R. E. W. & Lehrer, R. (1998) "Cationic peptides: a new source of antibiotics" *Trends Biotechnol* 16, 82-88.

Hancock. R. E. W. & Chapple, D. S. (1999) "Peptide antibiotics" *Antimicrob Agents Chemother* 43, 1317-1323.

Hancock, R. E. W. & Rozek, A. (2002) "Role of membranes in the activities of antimicrobial cationic peptides" *FEMS Microbiol Lett* 206, 143-149.

Hancock, R. E. W. Falla, T. & Brown, M. (1995) "Cationic bactericidal peptides" *Adv Microb Physio* 37, 135-175.

Helmerhorst, E. J., van't Hof, W., Veerman, E. C. I., Simoons-Smit, I. & Nieuw Amerongen, A. V. (1997) "Synthetic histatin analogues with broad-spectrum antimicrobial activity" *Biochem J* 326, 39-45.

Helmerhorst, E. J., Hodgson, R., van't Hof, W., Veerman, E. C. I., Allison, C. & Nieuw Amerongen, A. V. (1999) "The effects of histatin-derived basic antimicrobial peptides on oral biofilms" *J Dent Res* 78, 1245-1250.

Henderson, B., Poole, S. & Wilson, M. (editors) (1998) "Bacteria-Cytokine Interactions in Health and Disease" London: Portland Press.

Hong, S. V., Oh, J. E., Kwon, M., Choi, M. J., Lee, J. H., Lee, B. L, Moon, H. M. & Lee, K. H. (1998) "Identification and characterization of novel antimicrobial decapeptides generated by combinatorial chemistry" *Antimicrob Agents Chemother* 42, 2534-2541.

Kaiser, E., Colescott, R. L., Bossinger, C. D. & Cook, P. I. (1970) "Color test for detection of free terminal amino groups in the solid-phase synthesis of peptides" *Anal Biochem* 34, 595-598.

Kilian, M. Mikkelsen, L. & Henrichsen, J. (1989) "Taxonomic study of viridans streptococci: description of *Streptococcus gordonii* sp. novo and emended descriptions of *Streptococcus sanguis* (White and Niven 1946), *Streptococcus oralis* (Bridge and Sneath 1982), and *Streptococcus mitis* (Andrewes and Horder 1906)" *Int J Syst Bacterio* 139, 471-484.

Koczulla, A. R. & Bals, R. (2003) "Antimicrobial peptides: current status and therapeutic potential" *Drugs* 63, 389-406.

Koczulla, R., von Degenfeld, G., Kupaft, C. & 17 other authors (2003) "An angiogenic role for the human peptide antibiotic LL-37/hCAP-18" *J Clin Invest* 111, 1665-1672.

Kolenbrander, P. E. & London, J. (1992) "Ecological significance of coaggregation among oral bacteria" *Adv Microb Ecol* 12, 183-217.

Kolenbrander, P. E., Ganeshkumar, N., Cassels, F. J. & Hughes, C. V. (1993) "Coaggregation: specific adherence among human oral plaque bacteria" *FASEB J* 7, 406-413.

Lee, I. H., Cho, V. & Lehrer, R. I. (1997) "Effects of pH and salinity on the antimicrobial properties of clavanins" *Infect Immun* 65, 2898-2903.

Lisle, J. T., Stewart, P. S. & McFeters, G. A. (1999) "Fluorescent probes applied to physiological characterization of bacterial biofilms" *Methods Enzymol* 310, 166-178.

Loesche, W. J. & Syed, S. A. (1978) "Bacteriology of human experimental gingivitis: effect of plaque and gingivitis score" *Infect Immun* 21, 830-839.

MacKay, B. J., Denepitiya, L., Iacono, V. J., Krost, S. B. & Pollock, J. J. (1984) "Growth-inhibitory and bactericidal effects of human parotid salivary histidine-rich polypeptides on *Streptococcus mutans*" *Infect Immun* 44, 695-701.

Marsh, P. D., & Bradshaw D. J. (1995) "Dental plaque as a biofilm" *J Industrial Microbiol* 15, 169-175.

Mickels, N., McManus, C., Massaro, J. & 7 other authors (2001) "Clinical and microbial evaluation of a histatin-containing mouthrinse in humans with experimental gingivitis" *J Clin Periodontol* 28, 404-410.

Miyasaki, K. T., Bodeau, A. L., Selsted, M. E., Ganz, T. & Lehrer, R. I. (1990) "Killing of oral, gram-negative, facultative bacteria by the rabbit defensin, NP-1" *Oral Microbiol Immunol* 5, 315-319.

Miyasaki, K. T., Iofel, R. & Lehrer, R. I. (1997) "Sensitivity of periodontal pathogens to the bactericidal activity of synthetic protegrins, antibiotic peptides derived from porcine leukocytes" *J Dent Res* 76, 1453-1459.

Miyasaki, K. T., Iofel, R., Oren, A., Huynh, T. & Lehrer, R. I. (1998) "Killing of *Fusobacterium nucleatum*, *Porphyromonas gingivalis* and *Prevotella intermedia* by protegrins" *J Periodontal Res* 33, 91-98.

Mosca, D. A., Hurst, M. A., So, W., Viajar, B. S. C., Fujii, C. A. & Falla, T. J. (2000) "IB-367, a protegrin peptide with in vitro and in vivo activities against the microflora associated with oral mucositis" *Antimicrob Agents Chemother* 44, 1803-1808.

Mosmann, T. (1983) "Rapid calorimetric assay for cellular growth and survival: application to proliferation and cytotoxicity assays" *J Immunol Methods* 65, 55-63.

Murakami, M., Ohtake, T., Dorschner, R. A. & Gallo, R. L (2002) "Cathelicidin antimicrobial peptides are expressed in salivary glands and saliva" *J Dent Res* 81, 845-850.

Nizet, V., Ohtake, T., Lauth, X. & 7 other authors (2001) "Innate antimicrobial peptide protects the skin from invasive bacterial infection" *Nature* 414, 454-457.

Oh, J. E., Hong, S. V. & Lee, K. H. (1999) "Structure-activity relationship study: short antimicrobial peptides" *J Pept Res* 53, 41-46.

Pardi, A., Billeter, M. & Wuthrich, K. (1984) "Calibration of the angular dependence of the amide proton-C alpha proton coupling constants, 3JHN alpha, in a globular protein. Use of 3JHN alpha for identification of helical secondary structure" *J Mol Biol* 180, 741-751.

Raj, P. A., Edgerton, M. & Levine, M. J. (1990) "Salivary histatin 5: dependence of sequence, chain length, and helical conformation for candidacidal activity" *J Biol Chem* 265, 3898-3905.

Raj, P. A., Marcus, E. & Edgerton, M. (1996) "Delineation of an active fragment and poly(L-proline) II conformation for candidacidal activity of bactenecin 5" *Biochemistry* 35, 4314-4325.

Raj, P. A., Marcus, E. & Sukumaran, D. K. (1998) "Structure of human salivary histatin 5 in aqueous and nonaqueous solutions" *Biopolymers* 45, 51-67.

Raj, P. A., Karunakaran, T. & Sukumaran, D. K. (2000a) "Synthesis, microbicidal activity, and solution structure of the dodecapeptide from bovine neutrophils" *Biopolymers* 53, 281-292.

Raj, P. A., Antonyraj, K. J. & Karunakaran, T. (2000b) "Large-scale synthesis and functional elements for the antimicrobial activity of defensins" *Biochem J* 347, 633-641.

Rothstein, D. M., Spacciapoli, P., Tran, L. T., Xu, T., Roberts, F. D., Dalla Serra, M., Buxton, D. K., Oppenheim, F. G. & Friden, P. (2001) "Anticandida activity is retained in P-113, a 12-amino-acid fragment of histatin 5" *Antimicrob Agents Chemother* 45, 1367-1373.

Schutze, G. E., Kaplan, S. L & Jacobs, R. F. (1994) "Resistant *Pneumococcus*: a worldwide problem" *Infection* 22, 233-237.

Slots, J., Bragd, L, Wikström, M. & Dahlén, G. (1986) "The occurrence of *Actinobacillus actinomycetemcomitans*, *Bacteroides gingivalis* and *Bacteroides intermedius* in destructive periodontal disease in adults" *J Clin Periodontol* 13, 570-577.

Socransky, S. S., Haffajee, A. D., Cugini, M. A., Smith, C. & Kent, R. L, Jr (1998) "Microbial complexes in subgingival plaque" *J Clin Periodontol* 25, 134-144.

Summey, D. L. & Jordan, H. V. (1974) "Characterization of bacteria isolated from human root surface carious lesions" *J Dent Res* 53, 343-351.

Tamamura, H., Murakami, T., Horiuchi, S. & 7 other authors (1995) "Synthesis of protegrin-related peptides and their antibacterial and anti-human immunodeficiency virus activity" *Chem Pharm Bull (Tokyo)* 43, 853-858.

Tanaka, D., Miyasaki, K. T. & Lehrer, R. I. (2000) "Sensitivity of *Actinobacillus actinomycetemcomitans* and *Capnocytophaga* spp. to the bactericidal action of LL-37: a cathelicidin found in human leukocytes and epithelium" *Oral Microbiol Immunol* 15, 226-231.

van Houte, J. (1994) "Role of micro-organisms in caries etiology" *J Dent Res* 73, 672-681.

Wade, D., Andreu, D., Mitchell, S. A., Silveira, A. M., Boman, A., Boman, H. G. & Merrifield, R. B. (1992) "Antibacterial peptides designed as analogs or hybrids of cecropins and melittin" *Int J Pept Protein Res* 40, 429-436.

Wuthrich, K. (1986) "NMR of Proteins and Nucleic Acids" New York: Wiley.

Yeaman, M. R. & Yount, N. Y. (2003) "Mechanisms of antimicrobial peptide action and resistance" *Pharmacol Rev* 55, 27-55.

Zasloff, M. (1992) "Antibiotic peptides as mediators of innate immunity" *Curr Opin Immuno* 14, 3-7.

Zasloff, M. (2002) "Antimicrobial peptides of multicellular organisms" *Nature* 415, 389-395.

Zhao, C., Liu, L. & Lehrer, R. I. (1994) "Identification of a new member of the protegrin family by cDNA cloning" *FEBS Lett* 346, 285-288.

In the following description, reference is made to the accompanying drawings, and which is shown by way of illustration to the specific embodiments in which the invention may be practiced. The following embodiments are described in sufficient detail to enable those skilled in the art to practice the invention. It is to be understood that other embodiments may be utilized and that changes based on presently known methodology and/or functional equivalents may be made without departing from the scope of the invention.

Given the following detailed description, it should become apparent to the person having ordinary skill in the art that the invention herein provides novel methods for preventing the formation of biofilms and inhibiting the growth of oral microorganisms while mitigating problems of the prior art.

IV. BRIEF DESCRIPTION OF THE DRAWINGS AND PHOTOGRAPHS

The patent or application file contains at least one drawing executed in color. Copies of this patent or patent application publication with color drawing(s) will be provided by the Office upon request and payment of the necessary fee.

FIG. 2a is a summary of sequential and medium-range nuclear Overhauser effect (NOE) data from nuclear Overhauser effect spectroscopy (NOESY) spectra of KSL (peptide disclosed as SEQ ID NO: 1) recorded at 30° C. in H2O/2H2O using a mixing time of 150 minutes.

FIG. 2b is a summary of sequential and medium-range NOE data from NOESY spectra of KSL (peptide disclosed as SEQ ID NO: 1) recorded at 30° C. in (C2H3)2SO using a mixing time of 200 minutes.

FIG. 13a is a micrograph (magnification ×200) showing the reduction of oral biofilms formed by saliva bacteria on saliva-coated germanium discs after intermittent treatment (2 hr intervals) with culture medium.

FIG. 13b is a micrograph (magnification ×200) showing the reduction of oral biofilms formed by saliva bacteria on saliva-coated germanium discs after intermittent treatment (2 hr intervals) with medium containing the antimicrobial decapeptide KSL.

V. DETAILED DESCRIPTION

Figure 1A:
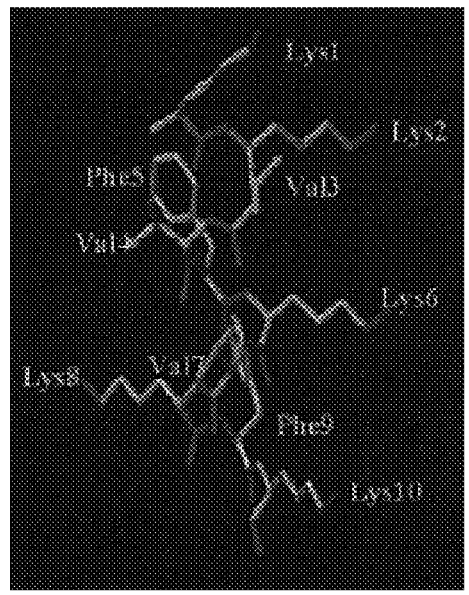
FIG. 1a is a perspective view of the α-helical structure of KSL.

Oral biofilms developed from saliva bacteria were used as a model to demonstrate the effects of the antimicrobial decapeptide KSL in accordance with the present invention in controlling the development of biofilms. Oral biofilms possess the characteristics that define biofilms in general. These characteristics include the adherence of the microbial organisms to surfaces, interfaces or to each other and are embedded in a matrix of extracellular polymeric substances that they have produced. In addition, biofilm cells exhibit altered phenotypes in regard to growth rate and gene transcription (Donlan et al., 2002). Further, oral biofilms or dental plaque represent one of the most widespread naturally occurring biofilms in humans and are associated with two of the most prevalent diseases affecting industrialized societies, namely dental caries and periodontal disease (Marsh et al., 1995).

The methods of the present invention are effective in preventing the formation of biofilms in environments comprising various microorganisms. For example, the methods of the present invention are effective in preventing the formation of biofilms which comprise microorganisms, including but not limited to *Fusobacterium nucleatum, Peptostreptococcus micros, Eubacterium timidum, Eubacterium brachy, Lactobacillus* spp., *Actinomyces naeslundii, Pseudomonas anaerobius, Eubacterium* sp. strain D8, *Prevotella intermedia, Fusobacterium* sp., *Selenomonas sputigena, Eubacterium* sp. strain D6, *Bacteroides pneumosintes, Haemophilus aphrophilus, Actinomyces israelli, S. mutans, S. gordonii, S. sanguis, S. oralis, S. sobrinus, S. salivarius, S. mitis, L. salivarius, Porphyromonas gingivalis, Tanerella forsythensis, Dialister pneumosintes, Veillonella parvula, L. acidophilus, Staphylococcus aureus* ATCC 6538, Methicillin-resistant *Staphylococcus aureus, Staphylococcus epidermidis* ATCC 12228, *Micrococcus luteus* ATCC 9341, *Mycobacterium smegmatis* ATCC 607, *Corynebacterium diphtheriae* ATCC 8024, *Escherichia coli* ATCC 2592, *Pseudomonas aeruginosa* ATCC 9027, *Proteus vulgaris* ATCC 6380, *Shigella flexneri* ATCC 203, or *Candida albicans* ATCC 36232.

The methods of the present invention are particularly effective in preventing the formation of biofilms that mimic supragingival or cariogenic plaque.

The methods of the present invention are also effective in inhibiting the growth of various oral microorganisms including, but not limited to *Fusobacterium nucleatum, Peptostreptococcus micros, Eubacterium timidum, Eubacterium brachy, Lactobacillus* spp., *Actinomyces naeslundii, Pseudomonas anaerobius, Eubacterium* sp. strain D8, *Prevotella intermedia, Fusobacterium* sp., *Selenomonas sputigena, Eubacterium* sp. strain D6, *Bacteroides pneumosintes, Haemophilus aphrophilus, Actinomyces israelli, S. mutans, S. gordonii, S. sanguis, S. oralis, S. sobrinus, S. salivarius, S. mitis, L. salivarius, Porphyromonas gingivalis, Tanerella forsythensis, Dialister pneumosintes, Veillonella parvula* or *L. acidophilus*.

Any carriers that are known to those having skill in the art may be used to administer the peptide of the present invention to the particular environment in accordance with the methods of the present invention. Examples of suitable commercially available carriers include, but are not limited to films or tapes, gels, microspheres such as hydrogel microspheres, lozenges, chewing gum, and dentifrices. The carrier may include a surfactant to assist in penetration of the peptide into the biofilm. In a preferred embodiment, the peptide is formulated in a chewing gum containing ingredients that include, but are not limited to a gum base, sodium bicarbonate as a gentle abrasive, sodium or stannous fluoride for enamel demineralization-remineralization cycles, xylitol as a natural sweetener, a surfactant, and flavoring such as peppermint flavor. The amount of peptide which is employed will vary depending upon the intended environment the peptide is administered to.

In addition to the determination of MICs and MBCs of KSL against oral bacteria, a bactericidal assay was performed, i.e. log reductions in viable counts, to obtain ED$_{99}$ values of KSL on selected organisms. These oral bacteria, which included *L. salivarius, S. mutans, S. gordonii* and *Actinobacillus actinomycetemcomitans*, showed significant reductions in viability (>3 logs) when exposed to KSL at concentrations of <10 µg ml$^{-1}$. With the exception of *Actinobacillus actinomycetemcomitans* [a causative agent for juvenile periodontitis (Slots et al., 1986)] and *S. gordonii*, our observations generally supported the MICs that were determined for these selected organisms. Interestingly, while KSL was less effective in inhibiting the growth of *Actinobacillus actinomycetemcomitans* and *S. gordonii*, as shown by the broth microdilution assay for MIC determinations, the peptide showed more potent inhibitory activity against the growth of these organisms in the bactericidal assay. These discrepancies could be attributable to the salinity of assay media used for determining the MICs and ED$_{99}$ of KSL, as indicated by a number of earlier reports on in vitro bactericidal activity of antimicrobial peptides (Lee et al., 1997; Friedrich et al., 1999; Tanaka et al., 2000; Guthmiller et al., 2001; Murakami et al., 2002; Zasloff, 2002).

Figure 1B:
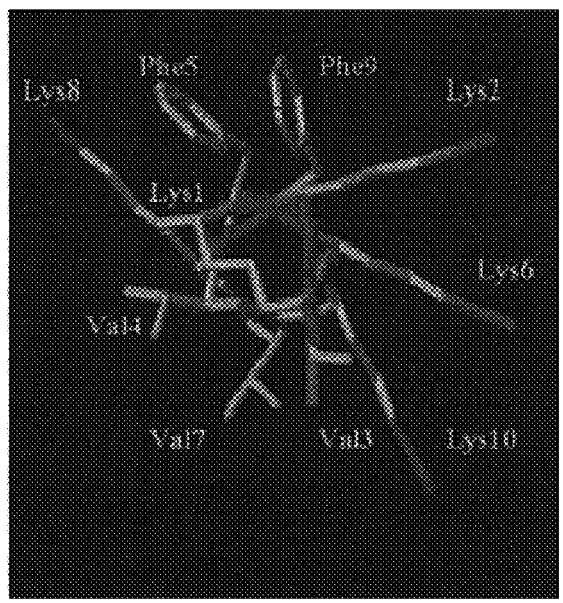
FIG. 1b is a perspective view of the α-helical structure of KSL along the helix axis.

The conformation of KSL in membrane environments was also established. The structure of the antimicrobial peptide used in the methods of the present invention is illustrated in FIGS. 1a and 1b. FIG. 1a displays the α-helical structure of KSL with the N-terminus at the top and the C-terminus at the bottom. FIG. 1b is a view of the α-helical structure of KSL along the helix axis. For clarity, hydrogen atoms are not included. The three dimensional structure of this antimicrobial peptide had not been reported previously, although the secondary structure of this peptide was predicted by circular dichroism (CD). Previous CD data suggested an α-helical conformation for KSL in the presence of 50% trifluoroethanol and a distorted α-helical structure in the presence of 25 mM sodium dodecyl sulfate (SDS) (Oh et al., 1999). However, determination of the helicity of small oligopeptides based on absolute mean ellipticity values often leads to ambiguous secondary structure prediction (Raj et al., 1990). Moreover, the conformational features of each individual residue in the sequence of the peptide cannot be ascertained and a clear distinction between α- and 3$_{10}$-helical structures cannot be made by CD data. Hence, the three-dimensional structure of KSL both in aqueous solution and in DMSO was determined, which mimics the polar aprotic membrane environment. As illustrated in FIG. 1, NMR data indicates that this peptide remains largely in its α-helical conformation in membrane environments, while it prefers to adopt an unfolded random structure in aqueous solution (not shown).

As shown in FIG. 1b, the view of the helical structure of KSL along the helix axis does not reflect a perfect amphiphilic structure. Enhancing amphiphilicity by the substitution of Lys1 and Lys8 by Leu residues has been reported to increase the helicity. However, antimicrobial activity has been found to decrease (Oh et al., 1999), thereby indicating the importance of cationic residues and the weak amphiphilicity of KSL. The weak amphiphilic nature of KSL indicates that its spontaneous insertion into microbial membranes and formation of ion channels across cell membranes is unlikely. This weak amphiphilicity probably accounts for the minimal toxicity to mammalian cells observed for KSL. This peptide is polar and hydrophilic, suggesting that the mechanism of its antimicrobial action could primarily involve electrostatic (ionic type), hydrogen bonding and hydrophobic interactions with the polar face of microbial membranes or with a membrane-bound receptor molecule, leading to possible membrane damage.

By using a BacLight Viabiilty kit, it was demonstrated that KSL could cause actual membrane damage to bacteria. This was illustrated by the presence of a significant number of organisms that fluoresced red in the KSL-treated saliva bacteria sample. SYTO 9, which is present in the assay solution, can enter all cells and fluoresces green. On the other hand, propidium iodide, which fluoresces red and is present as the second stain in the assay solution, is excluded from cells with intact membranes. However, propidium iodide is able to enter cells with a damaged membrane and competes with and quenches SYTO 9 for labeling the DNA, to make such cells fluoresce red (Lisle et al., 1999). The staining reactions of the bacteria that were observed provide strong morphological evidence to suggest that the membranes of KSL-treated bacteria were compromised, whereas membranes of bacteria exposed to $dH_2O$ remained intact, as illustrated by the presence of many green fluorescent bacteria in this sample.

Previous studies have shown that KSL is non-toxic to mammalian cells, as demonstrated by its lack of hemolytic activity against mouse erythrocytes (Hong et al., 1998). In the present invention, the in vitro toxicity study was confirmed and extended to include testing of KSL against human gingival fibroblasts (HGF). Our data indicated strongly that KSL neither induced cell death nor compromised the membrane integrity of HGF that were exposed to an up to tenfold excess of effective bactericidal dosages of this peptide. Similarly to other antimicrobial peptides (Hancock, 1997b; Zasloff, 2002), the results suggest that KSL specifically targets the membrane of prokaryotes, but not that of mammalian cells.

EXPERIMENTATION

EXAMPLE 1

Syntheses of the Antimicrobial Decapeptide KSL

KSL (lys-lys-val-val-phe-lys-val-lys-phe-lys (SEQ ID NO: 1) was synthesized by standard solid-phase procedures as described by Hong et al. (1998) by using 9-fluorenylmethoxycarbonyl (Fmoc) chemistry on an automatic peptide synthesizer (Model 90, Advanced ChemTech, Louisville, Ky.). The peptide was synthesized on Rink amide methylbenzhydrylamine (MBHA) resin (AnaSpec, San Jose, Calif.) with the first N-Fmocprotected Lys attached. The sequential coupling of protected Fmoc amino acid, which included Phe, Lys and Val, was done in N'-tetramethyluronium tetrafluoroborate (TBTU) (Advanced ChemTech) dissolved in N,N-dimethylforamide (DMF) (Advanced ChemTech) containing 0.55 M N,N'-diisopropylethylamine (DIEA) (Advanced ChemTech). Piperdine (20% v/v in DMF) was used to remove the N-terminal Fmoc moiety from the growing peptide prior to subsequent coupling. Completion of coupling reactions was assessed by the ninhydrin test of Kaise et al. Cleavage of the peptide from the resin and the deprotection of side chains were done by using a mixture of 95% trifluoroacetic acid and 5% ethane-dithiol. The synthetic peptides were purified by reverse-phase high-performance liquid chromatography (Hewlett-Packard, series 1100) using a Vydac C18 column. Peptide purity was confirmed by matrix-assisted laser desorption/ionization-time of flight (MALDI-TOF) mass spectrometry as performed by the laboratories of AnaSpec (San Jose, Calif.). The final product was stored in lyophilized form at −20° C. until use.

EXAMPLE 2

Nuclear Magnetic Resonance (NMR) Studies and Structural Analysis of KSL

The purified peptide (7 mg) was dissolved in 630 μl of double distilled water and 70 μl of $^2H_2O$ (Cambridge Isotope Laboratories, Woburn, Mass.) with peptide concentration being approximately 5 mM. The pH of the aqueous peptide solution was 3.8. For NMR experiments in dimethyl sulfoxide, the peptide (7 mg) was dissolved in 700 μl of 99.9% $(C^2H_3)_2SO$ (Cambridge Isotope Laboratories). The one dimensional (1D) and two dimensional (2D) NMR experiments used for conformational analyses were performed at 30° C. in these solvents. All NMR experiments were carried out at 500 MHz on a Varioa Unity Inova spectrometer equipped with a SUN Sparcstation 20. The 1 D-NMR spectra were recorded with a spectral width of 5000 Hz and a relaxation delay time of 2.5 seconds using 8 K data points zero filled to 32 K before Fourier transformation. All 2D experiments were multiplied by a phase-shifted sine bell function in both dimensions and zero-filled prior to Fourier transformation, in order to achieve appropriate resolution in each dimension. Nuclear Overhauser effect spectroscopy (NOESY), double quantum-filtered correlated spectroscopy (DQF-COSY) and total correlated spectroscopy (TOCSY) experiments were performed by using standard methods, as described in previous studies (Raj et al., 1998, 2000a). The coupling constant ($J_{NH-C\alpha H}$) values were determined either from the resolved 1D spectra (the digital resolution being 0.1 Hz) or from the high resolution DQF-COSY spectra. The hydrogen-deuterium ($^1H$-$^2H$) exchange of amide groups and variable temperature experiments were performed as described previously (Raj et al., 1998).

For structure calculation, the $^1H$-$^1H$ distances for structure determination were deduced from nuclear Overhauser effect (NOE) cross peak intensities in the 2D-NOESY spectrum obtained with 150 ms mixing time in water. The $C^{\beta H}/C^{\beta H'}$ cross peak of Phe5 was selected as the reference to calibrate the intensities against known distances. Dihedral φ angle restrains were obtained from the $J_{NH-c\alpha H}$ via the Karplus equation (Pardi et al., 1984). Structures were initially generated as described previously. A total of 135 NOE constraints, $d_{\alpha N}$(i, i+1), $d_{\alpha N}$(l, i), $d_{\alpha gamma}$(l, i+3), $d_{\alpha\alpha}$(l, i+1), and side-chain interproton distances were used as parameters for structure determination. Distance geometry calculations were performed on a Silicon Graphics 4D/35 workstation. Restrained energy minimization and structure analysis were carried out using the SYBYL 6.02 molecular modeling package (Tripos Associates, Inc., St. Louis, Mo.) on an Evans & Sutherland ESV3 workstation.

Sequential Resonance Assignments of KSL

Assignments of $^1$H resonances were accomplished by combined analyses of 2D TOCSY and 2D NOE spectra. Identification of most of the spin systems was achieved unambiguously from amide proton-relayed TOCSY connectivities. Assignment of resonances to individual amino acids was accomplished by combined analyses of the NH-CαH connectiviities in the fingerprint regions in the TOCSY and 2D NOE spectra, as described previously (Raj et al., 1996, 1998, 2000a).

Molecular Structure of KSL in dimethyl sulfoxide (DMSO) Solution

The average structure of a family of 16 conformers obtained after energy minimization of the distance geometry algorithm for NMR applications (DIANA) structures is shown in FIG. 1a. A view of the α-helical structure along the helix axis is also provided in FIG. 1b. The calculated mean pairwise root mean square deviation (RMSD) and the associated SDs are 1.78 (0.32) Å for all atoms and 1.12 (0.18) Å for the backbone (without taking into consideration the N-terminal residue, Lys1). When taking all residues into account, RMSDs are 2.38 (0.47) and 1.57 (0.26) Å for all atoms and backbone atoms, respectively. The structure of KSL is a single-stranded, α-helix stabilized by six intramolecular (5→1) hydrogen bonds formed by the backbone amide NH groups of Phe5-Lys10 (possible Coulombian interactions).

Conformational Analysis in Aqueous Solution

A summary of observed NOE connectivities, temperature coefficients of NH chemical shifts and coupling constant ($J_{NH-C\alpha H}$) values are provided in FIGS. 2a and 2b. Temperature coefficients of all amide resonances provided in FIG. 2a are high ($\geq 0.0042$ p.p.m. K$^{-1}$) and the fast $^1$H/$^2$H exchange rate observed for all backbone amide resonances (FIG. 2a) in 65% $^2$H$_2$O provides evidence that the amide groups are not involved in any intramolecular hydrogen bonding. Prevalence of strong αN (i, i+1) and weak αN (i, i) NOEs (FIG. 2a) and a continuous stretch of weak and medium βN (i, i) and αβ (i, i) NOEs (FIG. 2a) in the absence of any observable NN NOE interactions indicate that the backbone dihedral angles are predominantly in the unfolded extended region of the φ, ψ space. The $J_{NH-C\alpha H}$ values provided in FIG. 2a are $\geq 7.3$ Hz for all residues except Lys2 and Phe9. Coupling constants of 7.3-8.1 Hz were observed for most residues of KSL; this suggests the existence of populations of unfolded, non-hydrogen-bonded conformations of comparable energy with φ that exceed those of the regular helical region. The NMR data obtained provide evidence that KSL molecules remain unstructured in aqueous solution.

Conformational Analysis in DMSO Solution

In (C$^2$H$_3$)$_2$SO, lowered temperature coefficients of backbone amide groups ($\leq 0.0029$ p.p.m K$^{-1}$), except for the first four residues were observed as shown in FIG. 2b. These results suggest that six amide NH groups from Phe5 to Lys10 could be involved in intramolecular hydrogen bonding, whereas the amide NH groups of Lys2, Val3 and Val4 are well exposed to the solvent. As indicated in FIG. 2b, slow $^1$H/$^2$H exchange of the Phe5-Lys10 NH groups also suggests that the amide NHs of Phe5-Lys10 may be inaccessible to the solvent and are probably involved in intramolecular hydrogen bonds. In (C$^2$H$_3$)$_2$SO, the $J_{NH-C\alpha H}$ values were in the range of 5.2 to 5.9 Hz for residues from Phe5 to Lys10 (FIG. 2b), indicating the presence of a significant population of helical conformation in DMSO solution. The summary of sequential and medium range NOEs observed for KSL in (C$^2$H$_3$)$_2$SO shows sequential NN (i, i+1) connectivities and medium-range αβ (i, i+3) interactions that are characteristic of α-helical conformations. In addition, a complete set of weak αN (1, i+3) NOEs, expected for α-helical conformation, was observed. These NOE NN (1, i+1) values provide support for the prevalence of a threshold population of α-helical conformers that involve Lys2-Lys10, which are stabilized by six (5→1) intramolecular hydrogen bonds in (C$^2$H$_3$)$_2$SO.

Bacterial Strains for Examples 3-6

Strains used in Examples 3-6 included ATCC and laboratory strains of different oral bacteria. These included: *Actinomyces naeslundii* strain T14V-J1, *Actinomyces israelii* ATCC 10049, *Streptococcus mutans* strains LT 11 and ATCC 25175, *Streptococcus sobrinus* ATCC 33478, *Streptococcus gordonii* strains DL1 and ATCC 51656, *Streptococcus sanguis* strains SK36 and ATCC 10556, *Streptococcus salivarius* ATCC 9222, *Streptococcus oralis* strains 34 and ATCC 35037, *Lactobacillus salivarius* ATCC 29602, *Lactobacillus acidophilus* ATCC 4357, and *Actinobacillus actinomycetemcomitans* ATCC 43718. *S. mutans* strain LT 11 was kindly provided by Lin Tao, University of Illinois at Chicago, Ill. *S. gordonii* DLI, *S. sanguis* SK36, and *S. oralis* 34 were provided by John Cisar, National Institute of Dental and Craniofacial Research, NIH, Bethesda, Md.

EXAMPLE 3

Media, Culture Conditions and In Vitro Susceptibility Tests

Todd-Hewitt broth (THB), brain heart infusion (BHI) broth, Todd-Hewitt agar (THA), trypticase soy agar (TSA), lactobacilli MRS (MRS) broth, *Actinomyces* broth and Mueller-Hinton broth (MHB) were purchased from Becton Dickinson. Blood agar plates (BAP) were prepared by supplementing TSA with 5% sheep blood (PML Microbiologicals). All cultures, except for *Actinobacillus actinomycetemcomitans, S. mitis* and *Actinomyces israelii*, were grown at 37° C. in room air. *Actinobacillus actinomycetemcomitans* cultures were grown on BAP or in MHB supplemented with 15 µg haemin ml$^{-1}$ (Sigma), 15 µg β-nicotinamide adenine dinucleotide (NAD) ml$^{-1}$ (Sigma) and 5% yeast extract (Becton Dickinson) at 37° C. in 5% CO$_2$. *S. mitis* was grown on BAP or in BHI broth at 37° C. in 5% CO$_2$. *Actinomyces israeilli* was grown anaerobically in an anaerobic chamber (Coy Laboratory Products) in a 5% CO$_2$/10% H$_2$/85% N$_2$ atmosphere.

MICs were determined as described by Fuchs et al. (1998) with a slight modification. Procedures were based on the National Committee for Clinical Laboratory Standards broth microdilution method. MHB was used as the main assay medium for most of the tested organisms. Freshly grown cultures at exponential phase were used as the inoculum. Bacteria were centrifuged at 4000 r.p.m. for 15 min at 4° C., suspended in 2× concentrated medium and adjusted to 4×10$^6$ c.f.u ml−1 in 2× concentrated medium. Aqueous peptide solution (100 µl) was added to each well of a 96-well, flat-bottomed plate (Becton Dickinson). The peptide solution was serially diluted (twofold) with sterile distilled water in the wells, with final peptide concentrations ranging from 3.13 to 200 µg ml−1. After dispensing 100 µl aliquots of bacterial suspension into the wells, the 96-well plates were incubated at 37° C. for 24-48 h in room air, CO2 or anaerobically. The MIC was defined as the lowest concentration of the peptide that prevented visible turbidity, as measured at 600 nm by using an ELISA reader (Titertek Multiskan MCC/340). Visible turbidity was determined by the OD readings of tested samples that were significantly greater than that of the medium, i.e. background. Minimum bactericidal concentrations (MBCs) were determined by spiral-plating (Spiral Plater Autoplate 4000; Spiral Biotech) 50 µl from each clear well (≧MIC) onto BAP. After incubation for 24-48 h, the MBC was determined as the lowest concentration that did not permit visible growth on the surface of the agar. For the susceptibility study, small peptide at 200 µg ml−1, which had a sequence of LYPQPYQPQYQQYTF (SEQ ID NO: 2), and amoxicillin at 5 µg ml−1 were used as negative and positive controls, respectively. This control peptide was the C-terminal sequence (29-43) of salivary statherin, which showed no antimicrobial properties in previous studies (data not shown).

Results—In Vitro Susceptibility of Oral Bacteria

MICs and MBCs of KSL for the majority of oral bacteria tested in MHB or other modified broth were determined (See Table 1 below). MICs ranged from 3.13 to 100 µg ml$^{-1}$ for most of the facultative anaerobic oral organisms tested. By contrast, the control peptide at 200 µg ml$^{-1}$ did not inhibit the growth of any organisms tested. Bacteria grown in medium that contained the control peptide grew to the same extent as organisms grown in medium alone (data not shown). KSL was effective in inhibiting growth of most of the primary colonizers involved in the initiation of plaque formation, which included *Actimomyces naeslundii, S. gordonii* and *S. sanguis*, as demonstrated by the broth microdilution assay. Growth of the cariogenic bacteria *S. mutans* ATCC 25175$^T$, *S. sobrius* and *L. acidophilus* was also inhibited effectively by KSL concentrations of <25 µg ml$^{-1}$. On the other hand, KSL possessed less growth-inhibitory activity against *Actinobacillus actinomycetemcomitans* and *S. oralis*. In general, many of the MBCs of KSL for the organisms tested were within one to two dilutions of the MICs.

TABLE 1

In Vitro Susceptibility of Oral Bacteria to KSL

| Bacterial Strain* | MIC (µg ml$^{-1}$)† | MBC (µg ml$^{-1}$) |
|---|---|---|
| *Actinomyces naeslundii* T14V-J1 | 3.13 | 12.5 |
| *Actinomyces israelii* ATCC 10049 | 6.25 | 12.5 |
| *S. mutans* ATCC 25175† | 6.25 | 12.5 |
| *S. mutans* LT11 | 25 | 100 |
| *S. gordonii* ATCC 51656 | 50 | 100 |
| *S. gordonii* DL1 | 50 | 100 |
| *S. sanguis* ATCC 10556† | 25 | 100 |
| *S. sanguis* SK36 | 25 | 50 |
| *S. oralis* ATCC 35037† | 100 | 200 |
| *S. sobrinus* ATCC 33478† | 25 | 50 |
| *S salivarius* ATCC 9222 | 50 | 100 |
| *S. mitis* ATCC | 25 | 50 |
| *Actinobacillus actinomycetemcomitans* ATCC 43718 | 100 | 200 |
| *L. salivarius* ATCC 29602 | 3.13 | 12.5 |
| *L. acidophilus* ATCC 4357 | 3.13 | 12.5 |

*The number of cells used in these assays was $4 \times 10^6$ ml$^{-1}$, with the exception of *Actinobacillus* and *S. mutans* LT11, for which $4 \times 10^{7 \; ml-1}$ cells were used.
†MHB was used for the determination of most of the MICs. For *S. mitis* and *Actinobacillus*, BHI and 50% BHI were used as the assay medium, respectively. 10% MRS and 20% *Actinomyces* broth were used as the assay medium for *Lactobacillus* strains and *Actinomyces israelli*, respectively. Culture conditions were the same as those described in Example 3 above.

EXAMPLE 4

Bactericidal Assay

The bactericidal assay was performed according to procedures described by Miyasaki et al. (1997, 1998) with a slight modification. Briefly, bacterial suspension in Hanks' balanced salt solution (HBSS; Sigma), pH 7.0, or in 0.01% BHI (*Actinobacillus actinomycetecomitans*), was adjusted spectrophotometrically at 660 nm to approximately $1.0 \times 10^7$ cells ml$^{-1}$. Bacterial suspension (90 µl) was mixed with 10 µl KSL at different concentrations and the reactions were incubated at 37° C. for 15 min. The reaction was terminated by adding 900 µl ice-cold HBSS to the mixture and 50 µl of each sample was spiral-plated on agar media. Susceptibility was determined by examining the log reduction in viability counts of organisms that had been exposed to different concentrations of KSL. Bacteria suspended in HBSS served as a control. Bactericidal activity was also expressed as the 99% effective dose (ED$_{99}$), which is the concentration of the antimicrobial decapeptide at which there is a 2-log or more reduction in c.f.u. Four strains, *S. mutans* ATCC 25175$^T$, *S. gordonii* ATCC 51656, *Actinobacillus actinomycetemcomitans* ATCC 43718 and *L. salivarius* ATCC 29602, were tested for their susceptibility to KSL by the bactericidal assay.

Results—Bactericidal Assay (Reduction of Viable Counts)

Figure 3:
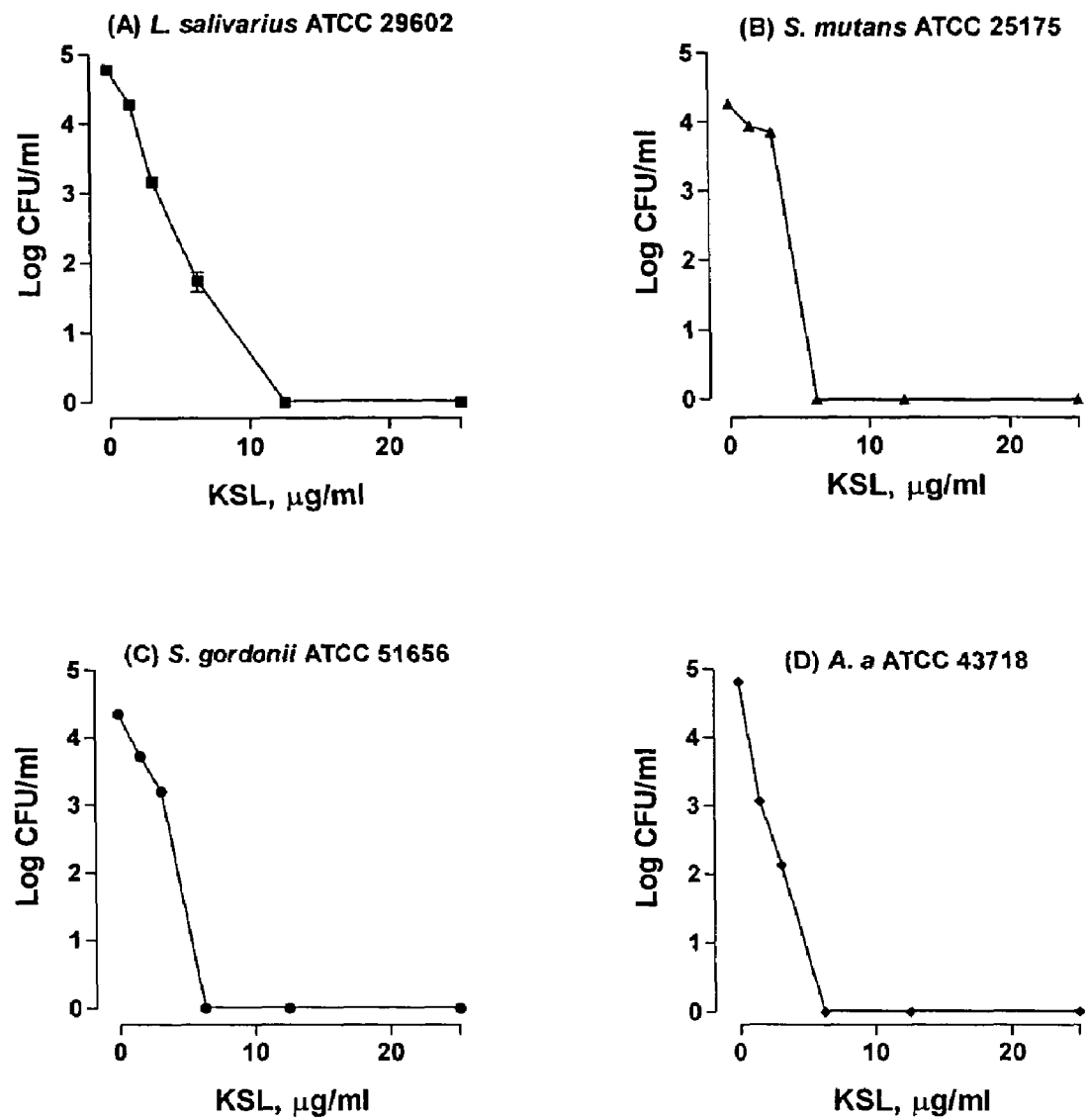
FIG. 3a is a graph showing the log reduction of viable counts of *L. salivarius* ATCC 29602 caused by KSL.
FIG. 3b is a graph showing the log reduction of viable counts of *S. mutans* ATCC 25175$^T$ caused by KSL.
FIG. 3c is a graph showing the log reduction of viable counts of *S. gordonii* ATCC 51656 caused by KSL.
FIG. 3d is a graph showing the log reduction of viable counts of *Actinobacillus actinomycetemcomitans* ATCC 43718 caused by KSL.

In addition to the determinations of MICs and MBCs of KSL, log reductions in viable counts of selected oral bacteria caused by KSL were also determined. These were compared to c.f.u. of organisms incubated in buffer, which served as controls (shown as 0 µg KSL ml$^{-1}$ in FIGS. 3a-3d). With the exception of *Actinobacillus actinomycetemcomitans*, for which the assays were performed in 0.01% BHI, bactericidal action of KSL was determined in isotonic HBSS after incubation with the targeted bacteria for 1 h at 37° C. KSL at 6.25 µg ml$^{-1}$, which was determined to be the 99% effective dose (ED$_{99}$), caused more than 2 log reductions in viable counts of the organisms tested, which included *L. salivarius* ATCC 29602 (FIG. 3a), *S. mutans* ATCC 25175$^T$ (FIG. 3b), *S. gordonii* ATCC 51656 (FIG. 3c), and *Actinobacillus actinomycetemcomitans* ATCC 43718 (FIG. 3d).

EXAMPLE 5

In Vitro Killing of Saliva Bacteria

The killing assay of saliva bacteria was done according to procedures established by Helmerhorst et al. (1999). Unstimulated saliva was collected from four healthy individuals who had refrained from eating for at least 2 hours. The study was approved by the Institutional Review Board of the Walter Reed Army Institute of Research and informed consent and sample donation consent were obtained from all volunteers. Pooled saliva was initially spun at 500 r.p.m. in an Eppendorf centrifuge (model 5810R) for 10 min at 4° C. to remove epithelial cells and mucus. Saliva bacteria were collected by spinning the supernatant at 4000 r.p.m. for 15 min at 4° C. The pellet was washed three times in 10 mM potassium phosphate buffer (PPB) and suspended in the same buffer to give approximately $1.0 \times 10^7$ cells ml$^{-1}$. Bacterial suspension (250 µl) was mixed with 250 µl peptide to obtain final peptide concentrations of 12.5, 25, 50, 100 and 200 µg ml$^{-1}$. After incubation of the mixture at 37° C. for 30 min, cells were spun down to remove KSL, washed once in PBS having a pH of 7.4 and suspended in PBS before spiral-plating 50 µl of the treated and untreated cells in different dilutions on BAP. The negative control was exposed to buffer only. Saliva bacteria exposed to 0.12% aqueous chlorhexidine served as positive controls.

Results—Viability of Saliva Bacteria Treated with KSL

Figure 4:
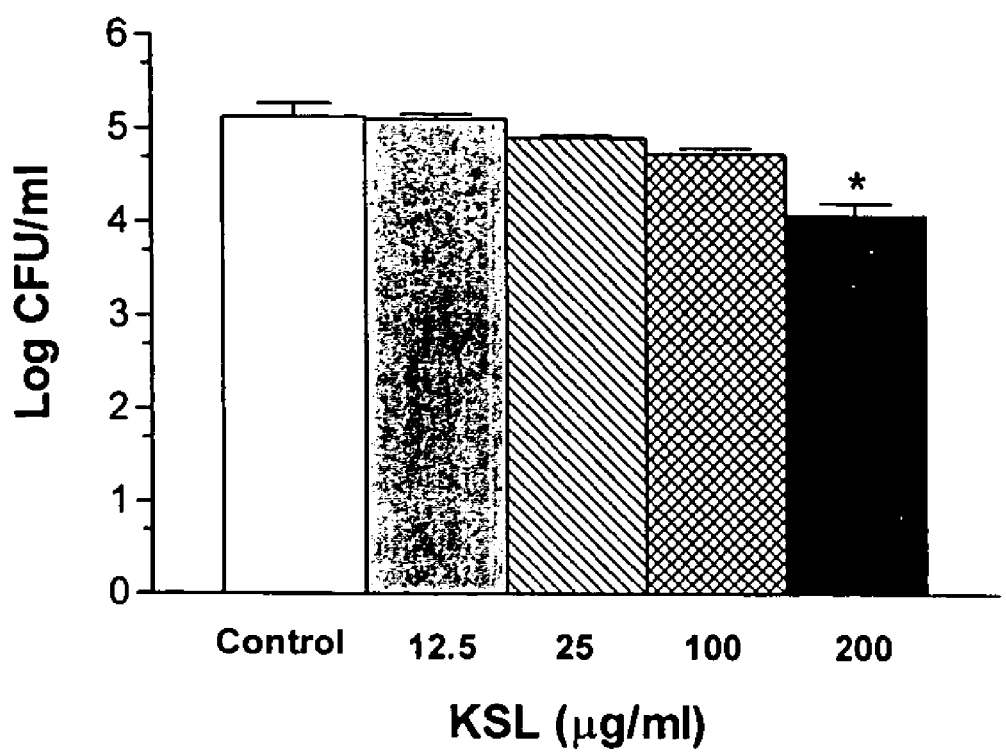
FIG. 4 is a graph showing the log reductions in colony forming units (c.f.u.) of facultative anaerobic bacteria collected from saliva after incubation for 30 min at 37° C.

As shown in FIG. 4, there was a significant reduction in viable counts of facultative anaerobic oral bacteria collected from saliva with exposure to increasing concentrations of KSL. A Mann-Whitney test was used for comparison of the experimental groups with the control group. The data respresent the results of one of the three separate experiments as described above, each performed in quadruplicate. The asterisk in FIG. 4 represents statistical significance from control (P<0.05). Treatment of the saliva bacteria with a final concentration of 200 µg KSL ml$^{-1}$ resulted in a 1.05 log reduction in facultative anaerobes that were present in the saliva, compared to PBS-treated saliva samples (negative control). As a positive control, chlorhexidine (0.12%) caused a >3 log reduction in facultative anaerobic saliva organisms (data not shown).

EXAMPLE 6

Assessing Viability of KSL-Treated Saliva Bacteria

A live/dead BacLight Bacterial Viability kit (Molecular Probes) was used to assess the viability and status of membrane integrity in saliva bacteria treated with aqueous KSL (200 µg ml$^{-1}$). A BacLight assay solution was prepared as described by the manufacturer. Saliva bacterial suspension in PPB (50 µl) was mixed with an equal volume of aqueous KSL to obtain a final peptide concentration of 200 µg ml$^{-1}$. Bacterial suspension mixed with sterile dH$_2$O was used as the negative control. BacLight solution (1.5 µl) was added to the mixture after incubation at 37° C. for 30 min. The reaction mixture was incubated further at room temperature in the dark for 15 min. Samples were observed by using a fluorescence Axioplan 2 imaging system (Zeiss) equipped with longpass and dual-emission filters (Chroma) for simultaneous viewing of live bacteria stained by SYTO 9, and dead bacteria stained by propidium iodide.

Results—Viability and Membrane Integrity of Saliva Bacteria Treated with KSL

Figure 5A:
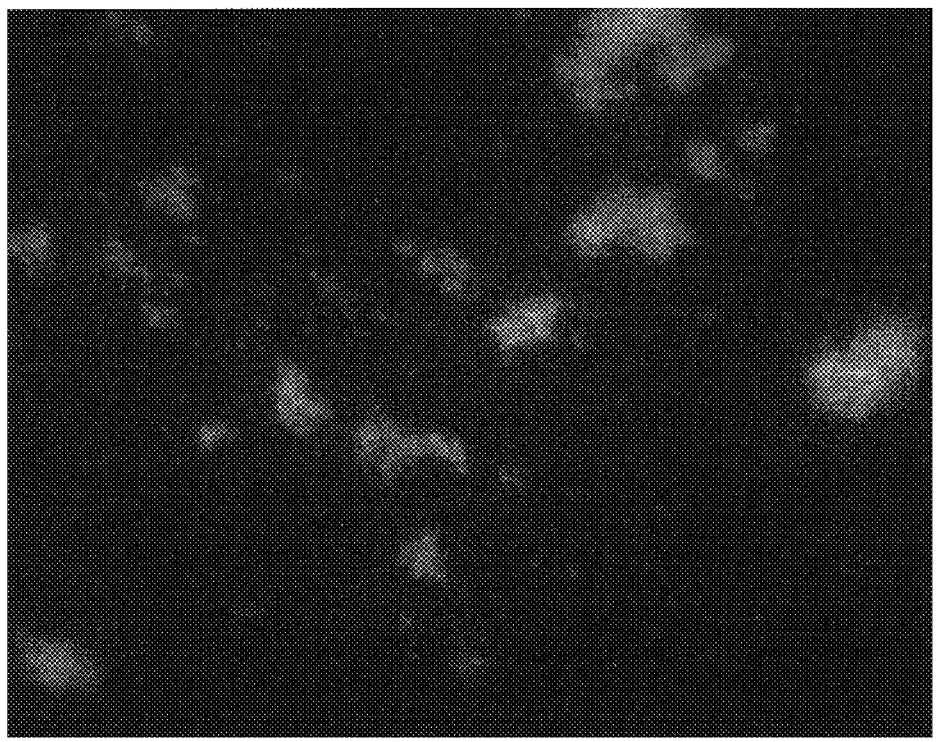
FIG. 5a is a photograph of live/dead BacLight staining of saliva bacteria treated with dH$_2$O (distilled water).
Figure 5B:
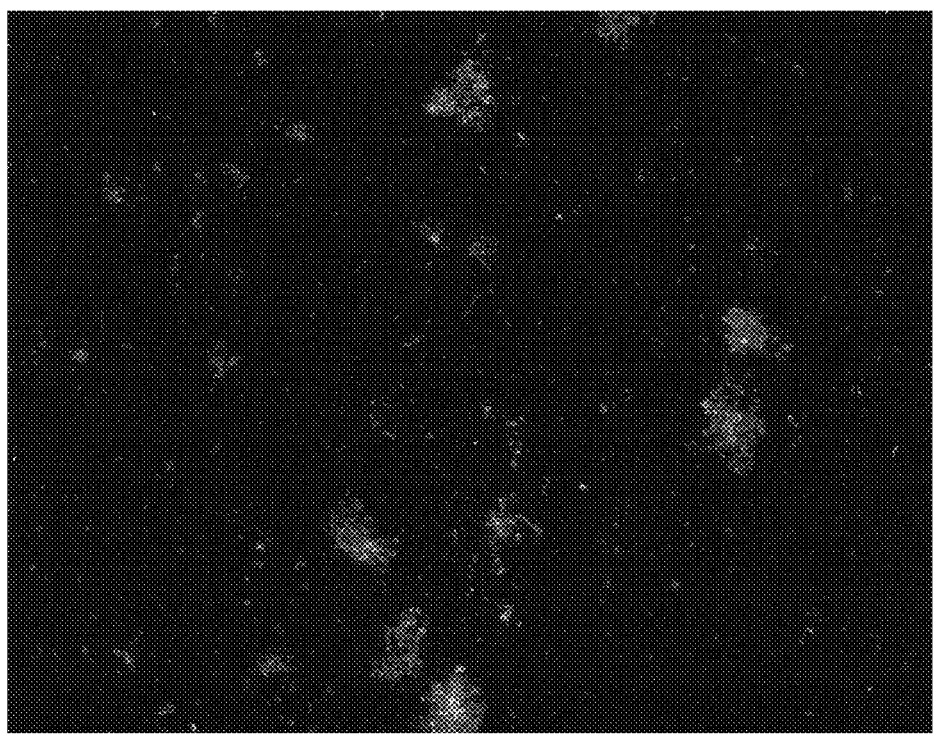
FIG. 5b is a photograph of live/dead BacLight staining of saliva bacteria treated with KSL.

Florescence microscopy of samples stained with live/dead BacLight assay solution showed that many of the saliva bacteria in the control sample (bacteria treated with dH$_2$O) fluoresced green as shown in FIG. 5a. On the other hand, bacterial suspension that had been treated with KSL showed a significant number of saliva bacteria that fluoresced red as illustrated in FIG. 5b.

EXAMPLE 7

In Vitro Toxicity Studies

HGF, obtained from the ATCC (Manassas, Va., USA) were used as the target for in vitro toxicity studies. HGF were cultured in RPMI 1640 medium (GibcoBRL) that contained 5% fetal bovine serum at 37° C. in a CO$_2$ incubator prior to exposure to various concentrations of KSL, which included concentrations that were at least tenfold (up to 1 mg ml$^{-1}$) above the effective antimicrobial doses used in the bactericidal assay. Cells that were exposed to medium alone served as controls. Untreated and affected cells were examined for viability, as determined by their ability to reduce 3-(4,5dimethylthiazol-2-yl)-2,5-diphenyltetrazolium bromide (MTT) (Sigma), and their membrane integrity, as a function of the amount of cytoplasmic lactate dehydrogenase (LDH) released into the medium. Detection of cellular conversion of MTT to water-insoluble coloured formazan and determination of total (cytoplasmic and extracellular) and extracellular LDH of affected and untreated cells were done according to the instructions of the manufacturer of a commercially available in vitro toxicity assay kit (Sigma). Reaction products of the LDH assay were measured spectrophotometrically by using a test wavelength of 490 nm and a reference wavelength of 690 nm. For measuring acid/isopropanol-solubilized formazan, a test wavelength of 570 nm and a reference wavelength of 630 nm were used.

Results—Viability of KSL-Treated HGF

Figure 6A:
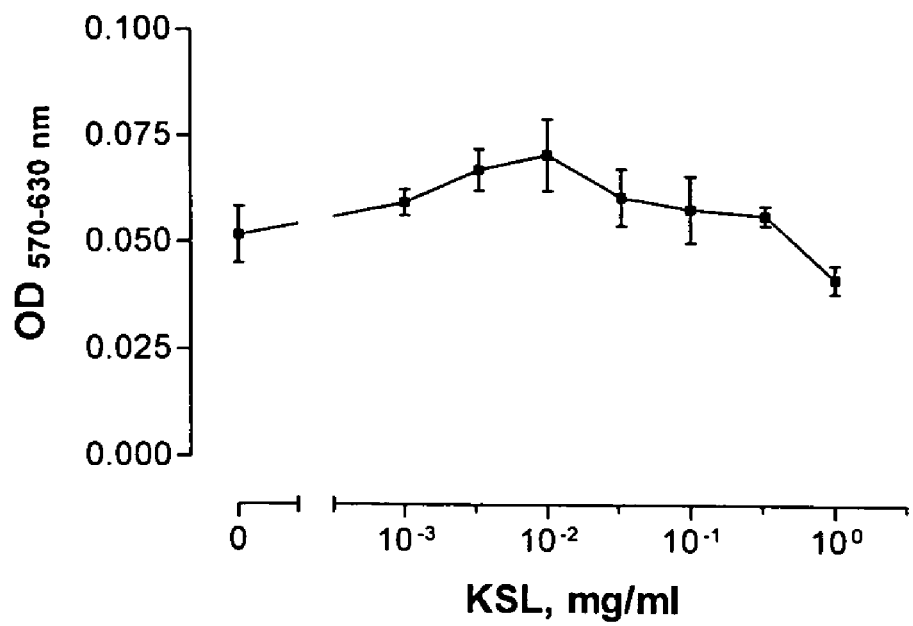
FIG. 6a is a graph showing similar levels of the reduction of MTT (indicative of metabolic active cells) by KSL-treated and untreated fibroblasts.
Figure 6B:
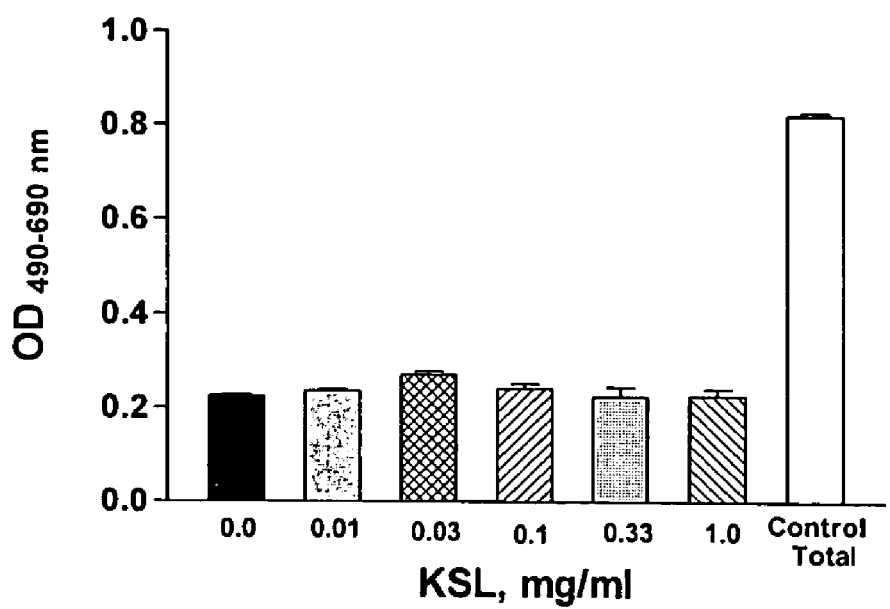
FIG. 6b is a graph showing minimal levels of LDH release by KSL-treated and untreated fibroblasts.

As indicated in FIG. 6a, KSL at concentrations up to 1 mg ml$^{-1}$ did not induce cell death of KSL-treated fibroblasts, as indicated by the ability of treated cells to reduce MTT at levels that were similar to those of untreated HGF. The points and bars in FIGS. 6a and 6b represent the mean and SD of triplicate determinations. Two thousand five hundred and ten thousand fibroblasts were used in each determination of LDH release and MTT reduction, respectively. Also, KSL did not compromise the membrane integrity of KSL-treated fibroblasts. As illustrated in FIG. 6b, similar levels of extracellular LDH were observed among KSL-treated cells and untreated HGF. HGF contained a significant amount of intracellular LDH, as indicated by the amount of total LDH recovered from lysed, untreated HGF (FIG. 6b)

EXAMPLE 8

Killing of Saliva Bacteria by KSL

Figure 7A:
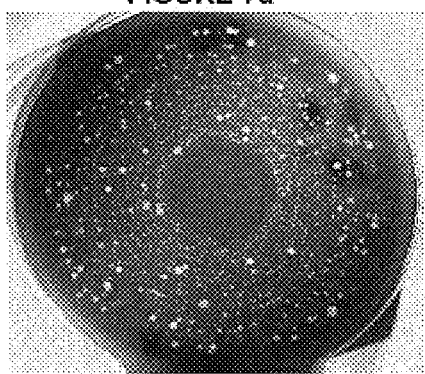
FIG. 7a is a photograph showing the effects of a control (phosphate buffered saline) on saliva bacteria isolated from human subjects for 30 min. at 37° C.
Figure 7B:
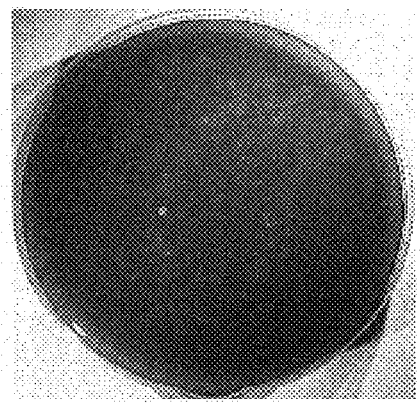
FIG. 7b is a photograph showing the effects of the antimicrobial decapeptide KSL on saliva bacteria isolated from human subjects for 30 min. at 37° C.

This example demonstrated, as revealed by colony reduction on blood agar plates, the killing of saliva bacteria isolated from human subjects by the antimicrobial decapeptide KSL. In a first (control) experiment, for which the results are shown in FIG. 7a, saliva bacteria were incubated with phosphate-buffered saline for 30 minutes at 37° C., serially diluted and spiral plated on a blood agar plate. In a second experiment, saliva bacteria were incubated with 200 µg/ml KSL for 30 minutes at 37° C., serially diluted and spiral plated on a blood agar plate. The results of the second experiment are shown in FIG. 7b. As compared to the treatment with phosphate-buffered saline, KSL caused significant reduction of colony forming units of tested bacteria.

Experimental Method for Examples 9-13

For Examples 9 through 13, the following procedure was used. Saliva was collected from four to six healthy human subjects and saliva bacteria were collected as described in Example 5. The collected bacteria pellet was washed three times in saliva buffer and resuspended with a small volume of 50% filter sterilized saliva. The resuspended saliva bacteria were then sonicated for 30 seconds two times to disrupt aggregates. This served as the saliva bacterial stock. The absorbance of the suspended saliva bacteria was adjusted to 0.05 at a wavelength of 600 nm by pipetting a small amount of saliva bacteria stock into 10-12 ml of 50% filter sterilized saliva. 50% sterile filtered saliva was used as the blank for adjustment. Hydroxyapatite discs were coated with 50% sterile saliva for 2 hours with slow shaking at room temperature in a 24 well microtiter plate. After two hours the saliva coated hydroxyapatite discs were removed and placed into a new 24 well microtiter plate. 1 ml of the saliva bacteria (OD$_{600\ nm}$ 0.05) was inoculated into each well containing a saliva-coated hydroxyapatite disc and incubated for 2 hours at 37° C. to allow the bacteria to attach to the disc surfaces.

EXAMPLE 9

Reduction of Colony-Forming Units of Oral Biofilms by KSL

Figure 8:
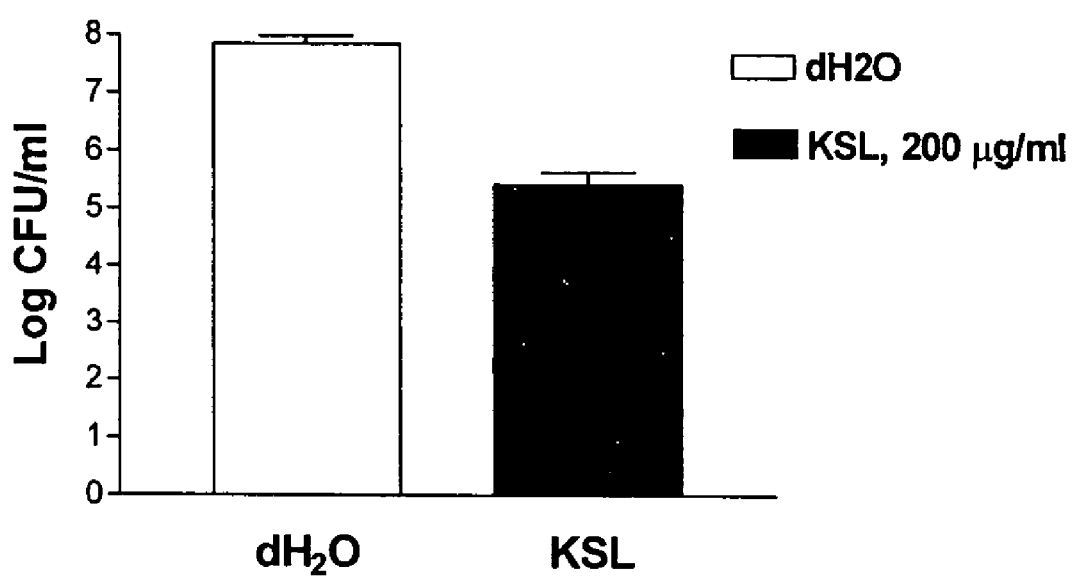
FIG. 8 is a graph illustrating the log reduction in colony-forming units of oral biofilm cells after pre-treatment with dH$_2$O or the antimicrobial decapeptide KSL for 30 min. at 37° C.

Example 9 illustrates the log reduction in colony-forming units of oral biofilm cells recovered from hydroxyapatite discs containing adherent saliva bacteria on their surfaces after pre-treatment with $dH_2O$ or the antimicrobial decapeptide KSL. In a first (control) experiment, saliva bacteria obtained from human subjects and adhered to hydroxyapetite surfaces were pre-treated with $dH_2O$ for 30 minutes at 37° C. prior to being incubated at 37° C. for 22 hours. In a second experiment, hydroxyapatite discs containing adherent saliva bacteria were pre-treated with KSL at a concentration of 200 µg/mL for 30 minutes at 37° C. and allowed to form biofilms for 22 hours at 37° C. Each experiment was conducted three separate times. The average result of each experiment is displayed in FIG. 8. KSL caused more than two log reductions of the viable counts of biofilm cells as compared to $dH_2O$ pre-treated samples.

EXAMPLE 10

Reduction of Biofilms Formed by Saliva Bacteria Pre-Treated with KSL

Figure 9:
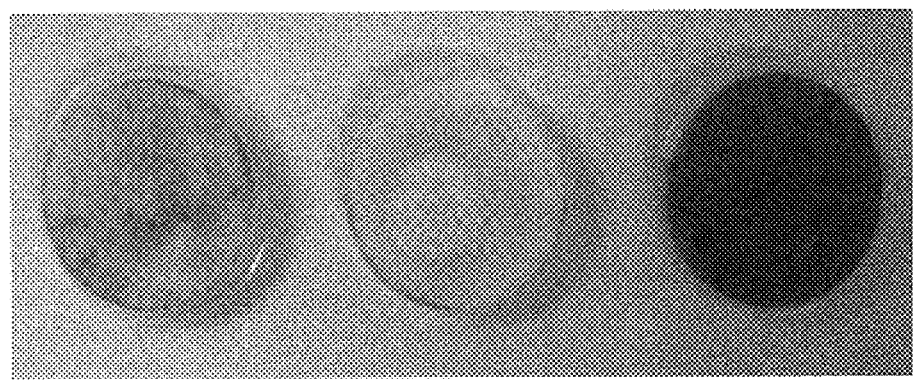
FIG. 9 is a photograph showing the reduction of biofilms formed by saliva bacteria on saliva-coated hydroxyapatite discs after pre-treatment with dH$_2$O or the antimicrobial decapeptide KSL.

The reduction of biofilms formed on saliva-coated hydroxyapatite discs was shown in this example. In a first (control) experiment, saliva bacteria obtained from human subjects and adhered to saliva coated hydroxyapatite discs at 37° C. for 2 hours, were pre-treated with $dH_2O$ and allowed to form biofilms for 22 hours at 37° C. In a second experiment, hydroxyapatite discs containing adherent saliva bacteria as described above were pre-treated with KSL and allowed to form biofilms for 22 hours at 37° C. A third uncoated hydroxyapatite disc having no saliva or bacteria cells was also analyzed. The presence of bioflims on each hydroxyapatite disc was shown by methylene blue (1%) staining. The results of each experiment are shown in FIG. 9. Abundant microcolonies (macroscopically shown as specks) of different sizes were found in the biofilm grown from the $dH_2O$ pre-treated discs whereas much fewer microcolonies were developed from the KSL-treated discs. The dark blue stained background shown on the hydroxyapatite disc treated with $dH_2O$ represents monolayers of adherent saliva bacteria. Macroscopically, there is a clear difference in color intensity and the appearance of specks between surfaces that contain biofilm cells as shown in the $dH_2O$ pre-treated (right) disc and those that are devoid of biofilm cells as demonstrated in the KSL pre-treated (left) disc and the uncoated (center) hydroxyapatite disc.

EXAMPLE 11

Figure 10A:
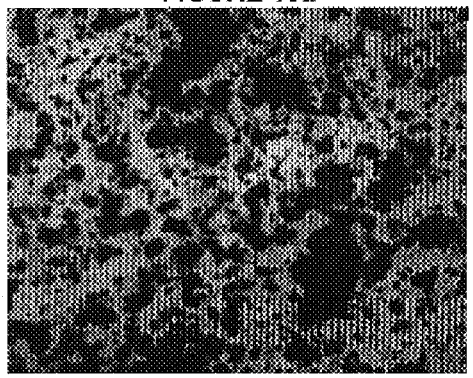
FIG. 10a is a micrograph (magnification ×100) of methylene blue stained biofilms which were developed from dH$_2$O pre-treated saliva bacteria.
Figure 10B:
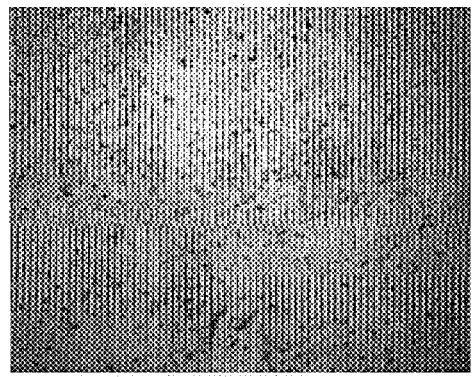
FIG. 10b is a micrograph (magnification ×100) of methylene blue stained biofilms which were developed from KSL pre-treated saliva bacteria.

Microscopic Examination of Reduction of Biofilms Formed by Saliva Bacteria Pre-Treated with KSL Microscopic examination of the biofilms grown in Example 10 from saliva bacteria pre-treated with $dH_2O$ (FIG. 10a) and KSL (FIG. 10b) was conducted. Magnification was ×100. The presence of monolayers of adherent bacteria and microcolonies were observed on the $dH_2O$ pre-treated $dH_2O$ discs. In contrast, there was an absence of adherent bacteria and microcolonies on the apatitic surface containing the saliva bacteria pre-treated with KSL.

EXAMPLE 12

Live/Dead Staining of Oral Biofilm Treated with KSL

Figure 11A:
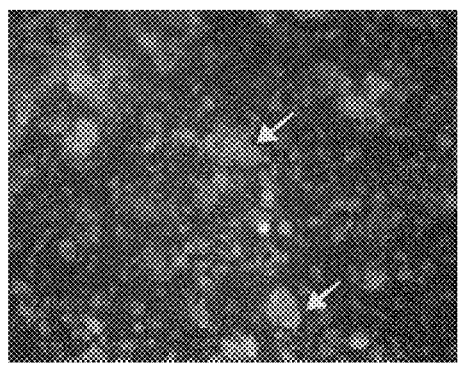
FIG. 11a is a micrograph (magnification ×100) showing a live/dead staining of an oral biofilm pre-treated with dH$_2$O.
Figure 11B:
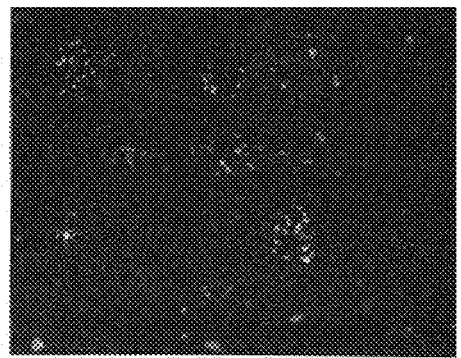
FIG. 11b is a micrograph (magnification ×100) showing a live/dead staining of an oral biofilm pre-treated with KSL.

Live/dead staining of the biofilms grown in Example 10 from saliva bacteria pre-treated with $dH_2O$ (FIG. 11a) and KSL (FIG. 11b) was conducted. Magnification was ×100. In the $dH_2O$ pre-treated sample, green fluorescent microcolonies, which indicated clusters of live biofilm cells, were abundant. This is indicated by the arrows in FIG. 11a. In contrast, a tremendous reduction of green microcolonies was found in biofilm cells pre-treated with KSL.

EXAMPLE 13

Figure 12:
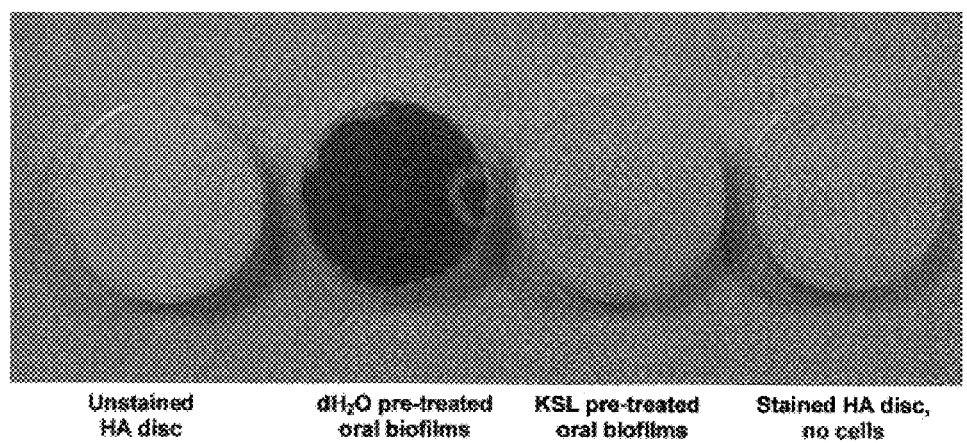
FIG. 12 is a photograph showing the reduction of biofilms formed by saliva bacteria on saliva-coated hydroxyapatite discs after pre-treatment with dH$_2$O or the antimicrobial decapeptide KSL for 45 hr at 37° C.

Reduction of Oral Biofilms by KSL as Revealed Macroscopically by Live/Dead Staining In a first (control) experiment, saliva bacteria obtained from human subjects and adhered to saliva-coated hydroxyapatite discs, were pre-treated with $dH_2O$ and allowed to form biofilms on a saliva-coated hydroxyapatite disc for 45 hours at 37° C. In a second experiment, saliva bacteria obtained from human subjects and adhered to saliva-coated hydroxyapatite discs as described above, were pre-treated with 200 µg/ml KSL and used to form biofilms for 45 hours at 37° C. A third uncoated hydroxyapatite disc having no saliva or bacteria cells was also analyzed. Each disc was stained with pink dye, which stains both live and dead bacteria. A fourth, unstained, uncoated hydroxyapatite disc having no saliva or bacteria was also analyzed. The results are illustrated in FIG. 12. The pre-treatment of saliva bacteria on hydroxyapatite discs with $dH_2O$ allowed for the confluent growth of biofilms. This is indicated by the strong presence of pink staining throughout the entire surface of this sample. In contrast, pre-treatment of biofilm cells with KSL significantly reduced the formation of oral biofilms by saliva bacteria as indicated by the lack of intense pink stain on the surface.

EXAMPLE 14

Reduction of Oral Biofilms as Revealed Microscopically in an In Vitro Plaque Model Treated with KSL Intermittently The reduction of oral biofilms formed on saliva-coated germanium discs was observed in-situ and in real time under the microscope using an in vitro flow cell model. In this experiment, saliva bacteria was obtained from human subjects and adhered to saliva-coated germanium discs. The bacteria were then allowed to form biofilms for 2 hours prior to receiving intermittent treatments (30 min treatment at 2 hr intervals) with culture medium (untreated) or KSL at 50 µg/ml (treated). The time-dependent development of biofilms on the saliva-coated germanium disks in the treated versus untreated groups was observed in situ by Differential Interference Contrast Microscopy. As shown in FIG. 13, there is a marked difference in the cell density and the structures of biofilms between the untreated (13a) and treated (13b) groups over time. After eight hours of incubation at 37° C. in the flow cells, the adherent saliva bacteria in the untreated group grew into film-like structures, which obliterate the entire surface of the discs. In contrast, the saliva bacteria in the group treated intermittently with KSL decapeptide grew sparsely with much of the surface area of the disc remaining unoccupied. The intermittent exposure of oral biofilms to the antimicrobials as shown in this study was intended to determine the effectiveness of some of the carriers (e.g., chewing gums or tablets), when used intermittently, for delivering the antimicrobial peptides to control biofilms which induce oral infections such as dental caries or periodontal diseases.

One of ordinary skill in the art armed with the teaching and examples of the present application can determine an effective amount for the methods of the present invention for a given antimicrobial agent.

Although only a few exemplary embodiments of the present invention have been described in detail above, those skilled in the art will readily appreciate that many modifications are possible without materially departing from the novel teachings and advantages of the present invention. Accordingly, all such modifications are intended to be included within the scope of the present invention as defined by the following claims.

terium sp., Selenomonas sputigena, Eubacterium sp. strain D6, Bacteroides pneumosintes, Haemophilus aphrophilus, Actinomyces israelli, S. mutans, S. gordonii, S. sanguis, S. oralis, S. sobrinus, S. salivarius, S. mitis, L. salivarius, Porphyromonas gingivalis, Tanerella forsythensis, Dialister pneumosintes, Veillonella parvula, L. acidophilus, Staphylococcus aureus ATCC 6538, Methicillin-resistant Staphylococcus aureus, Staphylococcus epidermidis ATCC 12228, Micrococcus luteus ATCC 9341, Mycobacterium smegmatis ATCC 607, Corynebacterium diphtheriae ATCC 8024, Escherichia coli ATCC 2592, Pseudomonas aeruginosa ATCC 9027, Proteus vulgaris ATCC 6380, Shigella flexneri ATCC 203, or Candida albicans ATCC 36232.

6. The method of claim 1, wherein the peptide is administered to the environment via topical application, spray, aerosol, injection, ingestion or inhalation.

7. The method of claim 6, wherein the peptide is administered to the environment in a carrier, and wherein the carrier is selected from the group consisting of films, tapes, gels, microspheres, lozenges, chewing gum, and dentifrices.

We claim:

1. A method of inhibiting biofilm formation in an environment comprising administering to the environment an effective amount of a peptide consisting of the amino acid sequence
NH$_2$-Lys-Lys-Val-Val-Phe-Lys-Val-Lys-Phe-Lys-CONH$_2$ (SEQ ID NO:1);
wherein the environment is a home, workplace, industrial environment, medical device, dental device, animal body or human body.

2. The method of claim 1, wherein the environment is a human body.

3. The method of claim 2, wherein the environment is a human mouth.

4. The method of claim 3, wherein the development of plaque or caries on a human tooth is prevented.

5. The method of claim 4, wherein the environment comprises microorganisms, and wherein the microorganisms are Fusobacterium nucleatum, Peptostreptococcus micros, Eubacterium timidum, Eubacterium brachy, Lactobacillus spp., Actinomyces naeslundii, Pseudomonas anaerobius, Eubacterium sp. strain D8, Prevotella intermedia, Fusobac- 8. The method of claim 7, wherein the carrier is chewing gum.

9. A method of inhibiting the growth of oral microorganisms comprising administering to an oral environment an effective amount of a peptide consisting of the amino acid sequence NH$_2$-Lys-Lys-Val-Val-Phe-Lys-Val-Lys-Phe-Lys-CONH$_2$ (SEQ ID NO:1).

10. The method of claim 9, wherein the oral microorganisms are Fusobacterium nucleatum, Peptostreptococcus micros, Eubacterium timidum, Eubacterium brachy, Lactobacillus spp., Actinomyces naeslundii, Pseudomonas anaerobius, Eubacterium sp. strain D8, Prevotella intermedia, Fusobacterium sp., Selenomonas sputigena, Eubacterium sp. strain D6, Bacteroides pneumosintes, Haemophilus aphrophilus, Actinomyces israelli, S. mutans, S. gordonii, S. sanguis, S. oralis, S. sobrinus, S. salivarius, S. mitis, L. salivarius, Porphyromonas gingivalis, Tanerella forsythensis, Dialister pneumosintes, Veillonella parvula or L. acidophilus.

11. The method of claim 9, wherein the oral environment is a human mouth.

12. The method of claim 11, wherein the method is used for the treatment or prevention of periodontitis, gingivitis or mucositis.

13. The method of claim 11, wherein the development of plaque or caries on a tooth is prevented.

14. The method of claim 9, wherein the peptide is administered to the environment via topical application, spray, aerosol, injection, ingestion or inhalation.

15. The method of claim 9, wherein the peptide is administered to the environment in a carrier, and wherein the carrier is selected from the group consisting of films, tapes, gels, microspheres, lozenges, chewing gum, and dentifrices.

16. The method of claim 15, wherein the carrier is chewing gum.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Syntheses of the Antimicrobial Decapeptide

<400> SEQUENCE: 1

Lys Lys Val Val Phe Lys Val Lys Phe Lys
1               5                   10